(12) United States Patent
Raksi

(10) Patent No.: US 12,016,799 B2
(45) Date of Patent: *Jun. 25, 2024

(54) INTEGRATED SURGICAL SYSTEM AND METHOD FOR TREATMENT IN THE IRIDO-CORNEAL ANGLE OF THE EYE

(71) Applicant: ViaLase, Inc., Aliso Viejo, CA (US)

(72) Inventor: Ferenc Raksi, Mission Viejo, CA (US)

(73) Assignee: ViaLase, Inc., Aliso Viejo, CA (US)

(*) Notice: Subject to any disclaimer, the term of this patent is extended or adjusted under 35 U.S.C. 154(b) by 559 days.

This patent is subject to a terminal disclaimer.

(21) Appl. No.: 17/003,805

(22) Filed: Aug. 26, 2020

(65) Prior Publication Data
US 2020/0390605 A1   Dec. 17, 2020

Related U.S. Application Data

(62) Division of application No. 16/036,833, filed on Jul. 16, 2018, now Pat. No. 10,821,023.

(51) Int. Cl.
*A61F 9/008*    (2006.01)
*A61F 9/007*    (2006.01)

(52) U.S. Cl.
CPC ...... *A61F 9/00825* (2013.01); *A61F 9/00781* (2013.01); *A61F 9/0084* (2013.01);
(Continued)

(58) Field of Classification Search
CPC .............. A61F 9/00825; A61F 9/00781; A61F 9/0084; A61F 2009/00851;
(Continued)

(56) References Cited

U.S. PATENT DOCUMENTS 5,549,596 A    8/1996  Latina
6,004,314 A *  12/1999 Wei .................... G01B 9/02089
                                                  606/18
(Continued)

FOREIGN PATENT DOCUMENTS

CN      104382689 B    9/2016
EP        1080706 A1   3/2001
(Continued)

OTHER PUBLICATIONS

PCT/US2019/039033, Int'l Search Report & Written Opinion (dated Oct. 2, 2019).

(Continued)

*Primary Examiner* — Mark W. Bockelman
(74) *Attorney, Agent, or Firm* — LOZA & LOZA, LLP; David S. Sarisky

(57) ABSTRACT

Intraocular pressure in an eye is reduced by delivering each of a high resolution optical coherence tomography (OCT) beam and a high resolution laser beam through the cornea, and the anterior chamber into the irido-corneal angle along an angled beam path. The OCT beam provides OCT imaging for diagnostic purposes and surgery planning and monitoring, while the laser beam is configured to modify tissue. A volume of ocular tissue within an outflow pathway in the irido-corneal angle is modified to reduce a pathway resistance present in one or more of the trabecular meshwork, the Schlemm's canal, and the one or more collector channels by applying the laser beam to ocular tissue defining the volume to thereby cause photo-disruptive interaction with the ocular tissue to reduce the pathway resistance or create a new outflow pathway.

20 Claims, 18 Drawing Sheets

(52) U.S. Cl.
CPC .............. *A61F 2009/00851* (2013.01); *A61F 2009/00855* (2013.01); *A61F 2009/00868* (2013.01); *A61F 2009/00872* (2013.01); *A61F 2009/00897* (2013.01)

(58) Field of Classification Search
CPC .. A61F 2009/00855; A61F 2009/00868; A61F 2009/00872; A61F 2009/00897; A61F 2009/00891
See application file for complete search history.

(56) References Cited

U.S. PATENT DOCUMENTS

| | | |
|---|---|---|
| 6,251,103 B1 | 6/2001 | Berlin |
| 6,482,199 B1 | 11/2002 | Neev |
| 6,682,523 B2 | 1/2004 | Shadduck |
| 6,989,007 B2 | 1/2006 | Shadduck |
| 7,131,968 B2 | 11/2006 | Bendett et al. |
| 7,192,412 B1 | 3/2007 | Zhou et al. |
| 7,282,046 B2 | 10/2007 | Simon |
| 7,351,241 B2 | 4/2008 | Bendett et al. |
| 7,771,417 B2 | 8/2010 | Telfair et al. |
| 8,011,504 B1 | 9/2011 | Farberov |
| 8,171,937 B2 | 5/2012 | Bendett et al. |
| 8,230,866 B2 | 7/2012 | Hauger et al. |
| 8,394,084 B2 | 3/2013 | Palankar et al. |
| 8,523,926 B2 | 9/2013 | Neev |
| 8,540,659 B2 | 9/2013 | Berlin |
| 8,568,393 B2 | 10/2013 | Palanker |
| 8,679,089 B2 | 3/2014 | Berlin |
| 8,687,866 B2 | 4/2014 | Marziliano et al. |
| 8,709,001 B2 | 4/2014 | Blumenkranz et al. |
| 8,845,624 B2 | 9/2014 | Raksi et al. |
| 8,920,407 B2 | 12/2014 | Raksi et al. |
| 9,033,963 B2 | 5/2015 | Vera et al. |
| 9,044,303 B2 | 6/2015 | Kurtz et al. |
| 9,101,448 B2 | 8/2015 | Blumenkranz et al. |
| 9,259,153 B2 | 2/2016 | Goto |
| 9,259,354 B2 | 2/2016 | Horvath et al. |
| 9,265,411 B2 | 2/2016 | Chen et al. |
| 9,271,870 B2 | 3/2016 | Palanker et al. |
| 9,301,878 B2 | 4/2016 | Raksi et al. |
| 9,320,650 B2 | 4/2016 | Bendett et al. |
| 9,441,946 B2 | 9/2016 | Massow et al. |
| 9,456,925 B2 | 10/2016 | Kurtz et al. |
| 9,474,648 B2 | 10/2016 | Palanker et al. |
| 9,498,295 B2 | 11/2016 | Palanker |
| 9,517,006 B2 | 12/2016 | Izatt et al. |
| 9,554,702 B2 | 1/2017 | Papac et al. |
| 9,560,963 B2 | 2/2017 | Buckland et al. |
| 9,603,741 B2 | 3/2017 | Berlin |
| 9,603,744 B2 | 3/2017 | Hailmann et al. |
| 9,629,750 B2 | 4/2017 | Dambacher et al. |
| 9,642,746 B2 | 5/2017 | Berlin |
| 9,681,985 B2 | 6/2017 | Andersen et al. |
| 9,724,238 B2 | 8/2017 | Heitel |
| 9,750,640 B2 | 9/2017 | Palanker et al. |
| 9,820,883 B2 | 11/2017 | Berlin |
| 9,833,357 B2 | 12/2017 | Berlin |
| 9,844,464 B2 | 12/2017 | Bendett et al. |
| 9,936,868 B2 | 4/2018 | Izatt et al. |
| 10,064,757 B2 | 9/2018 | Berlin |
| 10,073,515 B2 | 9/2018 | Awdeh |
| 10,159,600 B2 | 12/2018 | Horvath et al. |
| 10,159,601 B2 | 12/2018 | Berlin |
| 10,165,941 B2 | 1/2019 | Walsh et al. |
| 10,179,066 B2 | 1/2019 | Badawi et al. |
| 10,195,078 B2 | 2/2019 | Horvath et al. |
| 10,195,079 B2 | 2/2019 | Horvath et al. |
| 10,195,080 B2 | 2/2019 | Berlin |
| 10,238,281 B2 | 3/2019 | Isogai et al. |
| 10,238,541 B2 | 3/2019 | Yee et al. |
| 10,292,868 B2 | 5/2019 | Chew et al. |
| 10,335,314 B2 | 7/2019 | Berlin |
| 10,335,315 B2 | 7/2019 | Goldshleger et al. |
| 10,360,683 B2 | 7/2019 | Iwase et al. |
| 10,362,935 B2 | 7/2019 | Dastmalchi et al. |
| 10,362,936 B2 | 7/2019 | Buckland et al. |
| 10,363,169 B2 | 7/2019 | Belkin et al. |
| 10,363,172 B2 | 7/2019 | Kawai et al. |
| 10,383,689 B2 | 8/2019 | Berlin |
| 10,390,883 B2 | 8/2019 | Deladurantaye et al. |
| 10,398,306 B2 | 9/2019 | Liu |
| 10,406,034 B2 | 9/2019 | Siegele |
| 10,426,548 B2 | 10/2019 | Tearney et al. |
| 10,454,237 B2 | 10/2019 | Yu et al. |
| 10,456,030 B2 | 10/2019 | Buckland et al. |
| 10,456,209 B2 | 10/2019 | Peyman |
| 10,478,060 B2 | 11/2019 | Kubota |
| 10,493,274 B2 | 12/2019 | Irazoqui et al. |
| 10,499,809 B2 | 12/2019 | Kalina, Jr. et al. |
| 10,500,094 B2 | 12/2019 | Buzawa et al. |
| 10,517,760 B2 | 12/2019 | Berlin |
| 10,524,822 B2 | 1/2020 | Aljuri et al. |
| 10,537,476 B2 | 1/2020 | Ha et al. |
| 10,542,883 B2 | 1/2020 | Gooi et al. |
| 10,543,122 B2 | 1/2020 | Kahook |
| 10,543,123 B2 | 1/2020 | Neev |
| 10,568,763 B2 | 2/2020 | Vera et al. |
| 10,588,694 B1 | 3/2020 | Neev |
| 10,596,036 B2 | 3/2020 | Pinchuk |
| 10,603,214 B2 | 3/2020 | Bigler et al. |
| 10,603,216 B2 | 3/2020 | Kurtz et al. |
| 10,653,557 B2 | 5/2020 | Rill et al. |
| 10,674,906 B2 | 6/2020 | Kalina, Jr. et al. |
| 10,687,978 B2 | 6/2020 | Berlin |
| 10,702,416 B2 | 7/2020 | Belkin et al. |
| 10,744,033 B2 | 8/2020 | Baerveldt et al. |
| 10,744,034 B2 | 8/2020 | Homer |
| 10,758,418 B2 | 9/2020 | Vold et al. |
| 10,765,559 B2 | 9/2020 | Berlin |
| 10,779,988 B2 | 9/2020 | Fu et al. |
| 10,799,113 B2 | 10/2020 | Vadakke Matham et al. |
| 10,821,023 B2 | 11/2020 | Raksi |
| 10,821,024 B2 | 11/2020 | Raksi |
| 10,888,461 B2 | 1/2021 | Orthaber et al. |
| 10,898,381 B2 | 1/2021 | Bendett et al. |
| 11,019,996 B2 | 6/2021 | Kalina, Jr. et al. |
| 11,019,997 B2 | 6/2021 | Kalina, Jr. et al. |
| 11,026,860 B2 | 6/2021 | Andersen et al. |
| 11,039,958 B2 | 6/2021 | Berlin |
| 11,147,708 B2 | 10/2021 | Horvath et al. |
| 11,166,630 B2 | 11/2021 | Frisken et al. |
| 11,316,318 B2 | 4/2022 | Yu et al. |
| 11,376,160 B2 | 7/2022 | Romano et al. |
| 11,382,794 B2 | 7/2022 | Sacks et al. |
| 11,395,765 B2 | 7/2022 | Goldshleger et al. |
| 11,399,981 B2 | 8/2022 | Fu et al. |
| 2002/0013572 A1 | 1/2002 | Berlin |
| 2004/0070761 A1 | 4/2004 | Horvath et al. |
| 2006/0200113 A1 | 9/2006 | Haffner |
| 2008/0058781 A1 | 3/2008 | Langeweyde et al. |
| 2009/0012507 A1 | 1/2009 | Culbertson et al. |
| 2009/0118718 A1 | 5/2009 | Raksi et al. |
| 2009/0149840 A1 | 6/2009 | Kurtz |
| 2009/0149841 A1 | 6/2009 | Kurtz |
| 2009/0157062 A1 | 6/2009 | Hauger et al. |
| 2010/0130966 A1 | 5/2010 | Brownell |
| 2011/0092965 A1 | 4/2011 | Slatkine et al. |
| 2011/0172649 A1 | 7/2011 | Schuele et al. |
| 2011/0202046 A1 | 8/2011 | Angeley et al. |
| 2012/0257167 A1 | 10/2012 | Gille et al. |
| 2012/0259321 A1 | 10/2012 | Vera et al. |
| 2012/0283557 A1 | 11/2012 | Berlin |
| 2012/0303007 A1 | 11/2012 | Loesel et al. |
| 2013/0085484 A1 | 4/2013 | Van Valen et al. |
| 2013/0103011 A1 | 4/2013 | Grant et al. |
| 2013/0197634 A1 | 8/2013 | Palanker et al. |
| 2013/0237972 A1 | 9/2013 | Raksi |
| 2013/0289450 A1 | 10/2013 | Homer |
| 2014/0128853 A1 | 5/2014 | Angeley et al. |
| 2014/0142599 A1 | 5/2014 | Jeglorz et al. |
| 2014/0216468 A1 | 8/2014 | Goldshleger et al. |
| 2014/0236066 A1 | 8/2014 | Horvath et al. |

(56) References Cited

U.S. PATENT DOCUMENTS

| | | |
|---|---|---|
| 2014/0288485 A1 | 9/2014 | Berlin |
| 2014/0354951 A1 | 12/2014 | Izatt et al. |
| 2015/0077528 A1 | 3/2015 | Awdeh |
| 2015/0080783 A1 | 3/2015 | Berlin |
| 2015/0157505 A1 | 6/2015 | Neev |
| 2015/0202083 A1 | 7/2015 | Takeda et al. |
| 2015/0297408 A1 | 10/2015 | Dolzan et al. |
| 2015/0305939 A1 | 10/2015 | Vera et al. |
| 2015/0305940 A1 | 10/2015 | Vera et al. |
| 2015/0313759 A1 | 11/2015 | Vera et al. |
| 2015/0335477 A1 | 11/2015 | Schuele et al. |
| 2015/0359426 A1 | 12/2015 | Buckland et al. |
| 2016/0095751 A1 | 4/2016 | Berlin |
| 2016/0095752 A1 | 4/2016 | Srinivasan et al. |
| 2016/0213512 A1 | 7/2016 | Palanker et al. |
| 2016/0220110 A1 | 8/2016 | Vogler et al. |
| 2016/0367403 A1 | 12/2016 | Siewert et al. |
| 2017/0020732 A1 | 1/2017 | Berlin |
| 2017/0027437 A1 | 2/2017 | Neal et al. |
| 2017/0042736 A9 | 2/2017 | Berlin |
| 2017/0119579 A9 | 5/2017 | Berlin |
| 2017/0127938 A1 | 5/2017 | Izatt et al. |
| 2017/0202708 A1 | 7/2017 | Berlin |
| 2017/0326003 A1 | 11/2017 | Schuele et al. |
| 2018/0028355 A1 | 2/2018 | Raksi |
| 2018/0207029 A1 | 7/2018 | Herekar et al. |
| 2018/0221205 A1 | 8/2018 | Berlin |
| 2018/0235462 A1 | 8/2018 | Gooi et al. |
| 2018/0360310 A1 | 12/2018 | Berlin |
| 2018/0360655 A1 | 12/2018 | Berlin |
| 2019/0021908 A1 | 1/2019 | Scott |
| 2019/0083313 A1 | 3/2019 | Berlin |
| 2019/0083314 A1 | 3/2019 | Berlin |
| 2019/0117459 A1 | 4/2019 | Berlin |
| 2019/0240070 A1 | 8/2019 | Schmid et al. |
| 2019/0357768 A1 | 11/2019 | Shareef |
| 2020/0078218 A1 | 3/2020 | Holland et al. |
| 2021/0022921 A1 | 1/2021 | Berlin |
| 2021/0052416 A1 | 2/2021 | Herekar et al. |
| 2021/0298945 A1 | 9/2021 | Juhasz et al. |

FOREIGN PATENT DOCUMENTS

| | | |
|---|---|---|
| EP | 1208792 A1 | 5/2002 |
| EP | 1017308 B1 | 6/2003 |
| EP | 2384727 A1 | 11/2011 |
| JP | S58187911 A | 11/1983 |
| JP | 2005508704 A | 4/2005 |
| JP | 2015163193 A | 9/2015 |
| JP | 2016504964 A | 2/2016 |
| JP | 2016105827 A | 6/2016 |
| JP | 2016193033 A | 11/2016 |
| WO | 2013188885 A1 | 12/2013 |
| WO | 2017031570 A1 | 3/2017 |
| WO | 2018049246 A1 | 3/2018 |
| WO | 2019060756 A1 | 3/2019 |
| WO | 2019173759 A | 9/2019 |

OTHER PUBLICATIONS

PCT/US2019/039043, Int'l Search Report & Written Opinion (dated Oct. 10, 2019).
PCT/US2019/042553, Int'l Search Report & Written Opinion (dated Oct. 10, 2019).
PCT/US2019/042571, Int'l Search Report & Written Opinion (dated Oct. 15, 2019).
PCT/US2019/039033, IPEA Written Opinion (dated Jul. 6, 2020).
Brubaker, "Goldmann's equation and clinical measures of aqueous dynamics". Experimental Eye Research, vol. 78, Issue 3, pp. 633-637 (2004).
Grant, "Tonographic method for measuring the facility and rate of aqueous flow in human eyes". Arch. Ophthalmol. 44(2), pp. 204-214 (1950).
Hann et al. "Anatomic changes in schlemm's canal and collector channels in normal and primary open-angle glaucoma eyes using low and high perfusion pressures". Glaucoma, vol. 55:9 (Sep. 2014).
Johnstone, "The aqueous outflow system as a mechanical pump: evidence from examination of tissue and aqueous movement in human and non-human primates". J Glaucoma, vol. 13:5, pp. 421-438 (Oct. 2004).
Jones et al., "New methods of measuring the rate of aqueous flow in man with fluorescein". Experimental Eye Research, vol. 5:3, pp. 208-220 (Jul. 1966).
Junker et al. "Intraoperative optical coherence tomography and ab interno trabecular meshwork surgery with the trabectome." Clin Ophthalmol. 11: 1755-1760 (Sep. 28, 2017).
Kagemann et al. "Characterisation of Schlemm's canal cross-sectional area." Br J Ophthalmol 2014, 98 (Suppl. II) (Mar. 3, 2014).
McNabb et al. "Complete 360° circumferential gonioscopic optical coherence tomography imaging of the iridocorneal angle." Biomedical Optics Express vol. 6, Issue 4, pp. 1376-1391 (2015).
Rosenquist et al., "Ouflow resistance of enucleated human eyes at two different perfusion pressures and different extents of trabeculotomy". Current Eye Research, vol. 8:12, pp. 1233-1240 (1989).
Xin et al. "OCT study of mechanical properties associated with Trabecular meshwork and collector channel motion in human eyes." PLoS One. 2016; 11(9): e0162048. doi: 10.1371/journal.pone.0162048 (Sep. 6, 2016).
Xin et al. "Aqueous outflow regulation: optical coherence tomography implicates pressure-dependent tissue motion." Experimental Eye Research, vol. 158, pp. 171-186 (May 2017).
CA3106512 Office Action (dated Mar. 17, 2022).
JP 2021-526191 Office Action (dated May 10, 2022).
JP 2021-526191 Office Action (dated Nov. 15, 2022).
CA 3106512 Office Action (dated Nov. 21, 2022).
CA3106512 Office Action (dated Jun. 30, 2023).
Lumibird; "Optimis™ Fusion Next Generation SLY/YAG Laser"; Quantel Medical; Cournon d'Auvergne, France; 2020; 6 pgs.

* cited by examiner

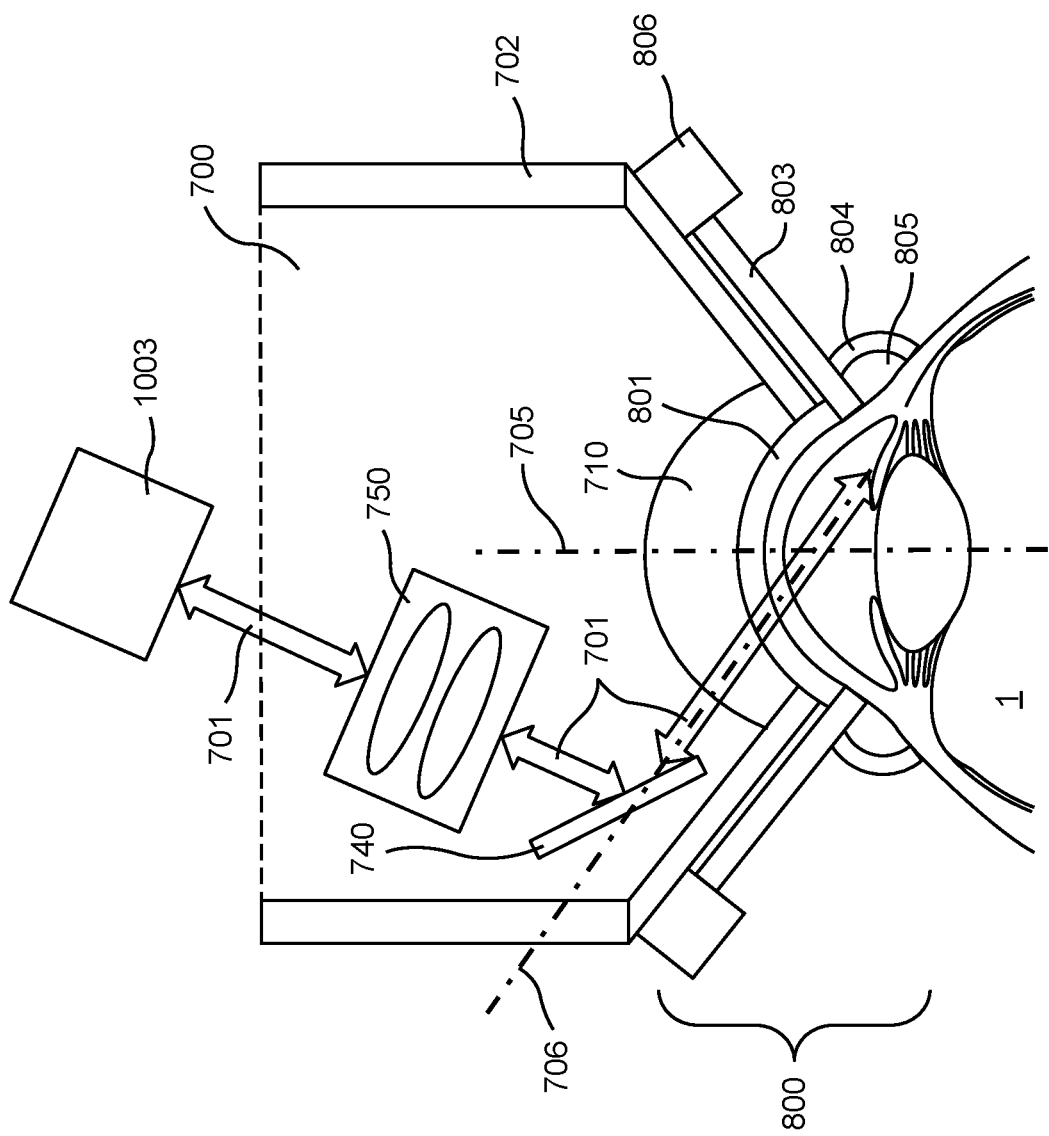

INTEGRATED SURGICAL SYSTEM AND METHOD FOR TREATMENT IN THE IRIDO-CORNEAL ANGLE OF THE EYE

CROSS-REFERENCE TO RELATED APPLICATION(S)

This application is a divisional application of U.S. patent application Ser. No. 16/036,833, filed Jul. 16, 2018, now U.S. Pat. No. 10,821,023, for "Integrated Surgical System and Method for Treatment in the Irido-Corneal Angle of the Eye," the entire disclosure of which is incorporated herein by reference.

TECHNICAL FIELD

The present disclosure relates generally to the field of medical devices and treatment of diseases in ophthalmology, and more particularly to systems, apparatuses, and methods for treatment of tissues, especially ocular tissue structures in the irido-corneal angle of the eye, for the laser surgery treatment of glaucoma.

BACKGROUND

Before describing the different types of glaucoma and current diagnosis and treatments options, a brief overview of the anatomy of the eye is provided.

Anatomy of the Eye

With reference to FIGS. 1-3, the outer tissue layer of the eye 1 includes a sclera 2 that provides the structure of the eye's shape. In front of the sclera 2 is a cornea 3 that is comprised of transparent layers of tissue that allow light to enter the interior of the eye. Inside the eye 1 is a crystalline lens 4 that is connected to the eye by fiber zonules 5, which are connected to the ciliary body 6. Between the crystalline lens 4 and the cornea 3 is an anterior chamber 7 that contains a flowing clear liquid called aqueous humor 8. Encircling the perimeter of the crystalline lens 4 is an iris 9 which forms a pupil around the approximate center of the crystalline lens. A posterior chamber 10 is located between the crystalline lens 4 and the retina 11. Light entering through the cornea 3 is optically focused through the crystalline lens 4.

With reference to FIG. 2, the corneoscleral junction of the eye is the portion of the anterior chamber 7 at the intersection of the iris 9 and the sclera 2. The anatomy of the eye 1 at the corneoscleral junction includes a trabecular meshwork 12. The trabecular meshwork 12 is a fibrous network of tissue that encircles the iris 9 within the eye 1. The base of the trabecular meshwork 12 and the edge of the iris 9 are attached together at the scleral spur 14. The network of tissue layers that make up the trabecular meshwork 12 are porous and thus present a pathway for the egress of aqueous humor 8 flowing from the anterior chamber 7. This pathway may be referred to herein as an aqueous humor outflow pathway, an aqueous outflow pathway, or simply an outflow pathway Referring to FIG. 3, the pathway formed by the pores in the trabecular meshwork 12 connect to a set of thin porous tissue layers called the uveal 15, the corneoscleral meshwork 16, and the juxtacanalicular tissue 17. The juxtacanalicular tissue 17, in turn, abuts a structure called Schlemm's canal 18. The Schlemm's canal 18 carries a mixture of aqueous humor 8 and blood from the surrounding tissue to drain into the venous system though a system of collector channels 19. As shown in FIG. 2, the vascular layer of the eye, referred to as the choroid 20, is next to the sclera 2. A space, called the suprachoroidal space 21, may be present between the choroid 20 and the suprachoroidal space 21. The general region near the periphery of the wedge between the cornea 3 and the iris 9, running circumferentially is called the irido-corneal angle 13. The irido-corneal angle 13 may also be referred to as the corneal angle of the eye or simply the angle of the eye. The ocular tissues illustrated in FIG. 3 are all considered to be within the corneal angle 13.

With reference to FIG. 4, two possible outflow pathways for the movement of aqueous humor 8 include a trabecular outflow pathway 40 and a uveoscleral outflow pathway 42. Aqueous humor 8, which is produced by the ciliary body 6, flows from the posterior chamber 10 through the pupil into the anterior chamber 7, and then exits the eye through one or more of the two different outflow pathways 40, 42. Approximately 90% of the aqueous humor 8 leaves via the trabecular outflow pathway 40 by passing through the trabecular meshwork 12, into the Schlemm's canal 18 and through one or more plexus of collector channels 19 before draining through a drain path 41 into the venous system. Any remaining aqueous humor 8 leaves primarily through the uveoscleral outflow pathway 42. The uveoscleral outflow pathway 42 passes through the ciliary body 6 face and iris root into the suprachoroidal space 21 (shown in FIG. 2). Aqueous humor 8 drains from the suprachoroidal space 21, from which it can be drained through the sclera 2.

Aqueous humor 8 outflow through the trabecular outflow pathway 40 is pressure dependent in that outflow increase as the intraocular pressure increases, whereas aqueous humor 8 outflow through the uveoscleral outflow pathway 42 is pressure independent. Resistance to the outflow of aqueous humor 8 through the trabecular outflow pathway 40 may lead to elevated intra-ocular pressure of the eye, which is a widely recognized risk factor for glaucoma. Resistance through the trabecular outflow pathway 40 may increase due to a collapsed Schlemm's canal 18 or the presence of a high density of collector channels 19.

Referring to FIG. 5, as an optical system, the eye 1 is represented by an optical model described by idealized centered and rotationally symmetrical surfaces, entrance and exit pupils, and six cardinal points: object and image space focal points, first and second principal planes, and first and second nodal points. Angular directions relative to the human eye are often defined with respect to an optical axis 24, a visual axis 26, a pupillary axis 28 and a line of sight 29 of the eye. The optical axis 24 is the symmetry axis, the line connecting the vertices of the idealized surfaces of the eye. The visual axis 26 connects the foveal center 22 with the first and second nodal points to the object. The line of sight 29 connects the fovea through the exit and entrance pupils to the object. The pupillary axis 28 is normal to the anterior surface of the cornea 3 and directed to the center of the entrance pupil. These axes of the eye differ from one another only by a few degrees and fall within a range of what is generally referred to as the direction of view.

Glaucoma

Glaucoma is a group of diseases that can harm the optic nerve and cause vision loss or blindness. It is the leading cause of irreversible blindness. Approximately 80 million people are estimated to have glaucoma worldwide and of these, approximately 6.7 million are bilaterally blind. More than 2.7 million Americans over age 40 have glaucoma. Symptoms start with loss of peripheral vision and can progress to blindness.

There are two forms of glaucoma, one is referred to as closed-angle glaucoma, the other as open-angled glaucoma. With reference to FIGS. 1-4, in closed-angle glaucoma, the iris 9 in a collapsed anterior chamber 7 may obstruct and close off the flow of aqueous humor 8. In open-angle glaucoma, which is the more common form of glaucoma, the permeability of ocular tissue may be affected by blockage of tissue in the irido-corneal angle 13 along the trabecular outflow pathway 40 or by the collapse of the Schlemm's canal 18 or collector channels 19.

As previously stated, elevated intra-ocular pressure (IOP) of the eye, which damages the optic nerve, is a widely recognized risk factor for glaucoma. However, not every person with increased eye pressure will develop glaucoma, and glaucoma can develop without increased eye pressure. Nonetheless, it is desirable to reduce elevated IOP of the eye to reduce the risk of glaucoma.

Methods of diagnosing conditions of the eye of a patient with glaucoma include visual acuity tests and visual field tests, dilated eye exams, tonometry, i.e. measuring the intra-ocular pressure of the eye, and pachymetry, i.e. measuring the thickness of the cornea. Deterioration of vision starts with the narrowing of the visual field and progresses to total blindness. Imaging methods include slit lamp examination, observation of the irido-corneal angle with a gonioscopic lens and optical coherence tomography (OCT) imaging of the anterior chamber and the retina Once diagnosed, some clinically proven treatments are available to control or lower the intra-ocular pressure of the eye to slow or stop the progress of glaucoma. The most common treatments include: 1) medications, such as eye drops or pills, 2) laser surgery, and 3) traditional surgery. Treatment usually begins with medication. However, the efficacy of medication is often hindered by patient non-compliance. When medication does not work for a patient, laser surgery is typically the next treatment to be tried. Traditional surgery is invasive, more high risk than medication and laser surgery, and has a limited time window of effectiveness. Traditional surgery is thus usually reserved as a last option for patients whose eye pressure cannot be controlled with medication or laser surgery.

Laser Surgery

With reference to FIG. 2, laser surgery for glaucoma target the trabecular meshwork 12 to decrease aqueous humor 8 flow resistance and increase aqueous humor outflow. Common laser treatments include Argon Laser Trabeculoplasty (ALT), Selective Laser Trabeculoplasty (SLT) and Excimer Laser Trabeculostomy (ELT).

ALT was the first laser trabeculoplasty procedure. During the procedure, an argon laser of 514 nm wavelength is applied to the trabecular meshwork 12 around 180 degrees of the circumference of the irido-corneal angle 13. The argon laser induces a thermal interaction with the ocular tissue that produces openings in the trabecular meshwork 12. ALT, however, causes scarring of the ocular tissue, followed by inflammatory responses and tissue healing that may ultimately close the opening through the trabecular meshwork 12 formed by the ALT treatment, thus reducing the efficacy of the treatment. Furthermore, because of this scarring, ALT therapy is typically not repeatable.

SLT is designed to lower the scarring effect by selectively targeting pigments in the trabecular meshwork 12 and reducing the amount of heat delivered to surrounding ocular tissue. During the procedure, a solid state laser of 532 nm wavelength is applied to the trabecular meshwork 12 between 180 to 360 degrees around the circumference of the irido-corneal angle 13 to produce openings through the trabecular meshwork 12. SLT treatment can be repeated, but subsequent treatments have lower effects on IOP reduction.

ELT uses a 308 nm wavelength ultraviolet (UV) excimer laser and non-thermal interaction with ocular tissue to treat the trabecular meshwork 12 in a manner that does not invoke a healing response. Therefore, the IOP lowering effect lasts longer. However, because the UV light of the laser cannot penetrate deep into the eye, the laser light is delivered to the trabecular meshwork 12 via an optical fiber inserted into the eye 1 through an opening and the fiber is brought into contact with the trabecular meshwork. The procedure is highly invasive and is generally practiced simultaneously with cataract procedures when the eye is already surgically open. Like ALT and SLT, ELT also lacks control over the amount of IOP reduction.

None of these existing laser treatments represents an ideal treatment for glaucoma. Accordingly, what is needed are systems, apparatuses, and method for laser surgery treatment of glaucoma that effectively reduce IOP without significant scarring of tissue, so the treatment may be completed in a single procedure and repeated at a later time if necessary.

SUMMARY

The present disclosure relates to a method of reducing intraocular pressure in an eye having a cornea, an anterior chamber, and an irido-corneal angle comprising an aqueous humor outflow pathway formed of a trabecular meshwork, a Schlemm's canal, and one or more collector channels branching from the Schlemm's canal. The method includes delivering each of an optical coherence tomography (OCT) beam and a laser beam through the cornea, and the anterior chamber into the irido-corneal angle. The method further includes modifying a volume of ocular tissue within the outflow pathway to reduce a pathway resistance present in one or more of the trabecular meshwork, the Schlemm's canal, and the one or more collector channels by applying the laser beam to ocular tissue defining the volume to thereby cause photo-disruptive interaction with the ocular tissue to reduce the pathway resistance or create a new outflow pathway.

In an aspect of this method, each of an OCT beam and a laser beam are delivered to the irido-corneal angle by directing each beam to a first optical subsystem that includes a window coupled to the cornea and an exit lens coupled to the window. The eye, by nature, comprises a direction of view and the first optical subsystem is characterized by a first optical axis that is substantially aligned with the direction of view when the first optical system is coupled to the eye. Distortion and refraction of the beams along the way to the irido-corneal angle are compensated for by directing each beam into the first optical subsystem along a second optical axis offset from the first optical axis by an angle α. The exit lens comprises a convex surface and distortion and refraction is further compensated for by directing each beam into the convex surface of the exit lens at an angle β relative to a surface normal to the convex surface.

In further aspects of the method, the OCT beam and the laser beam may be collinearly directed or non-collinearly directed to the first optical subsystem. The OCT beam is configured to provide high resolution images, while the laser beam is configured to provide high precision tissue modification. To this end, each beam may have substantially equal resolutions, on the order of approximately 5 micrometers. The laser beam is configured to initiate disruptive interaction with the ocular tissue to creates a channel opened through the trabecular meshwork connecting the anterior chamber and the Schlemm's canal. To this end, the laser beam may have a wavelength between 330 nanometers and 2000 nanometers and may be delivered as a multitude of laser pulses with pulse duration between 20 femtoseconds and 1 nanosecond.

The present disclosure also relates to an integrated surgical system for reducing intraocular pressure in an eye having a cornea, an anterior chamber, and an irido-corneal angle comprising an aqueous humor outflow pathway formed of a trabecular meshwork, a Schlemm's canal, and one or more collector channels branching from the Schlemm's canal. The system includes a first optical subsystem, a second a first optical subsystem, and a control system. The a first optical subsystem includes a window configured to be coupled to the cornea, and an exit lens configured to be coupled to the window. The second optical subsystem includes an OCT imaging apparatus configured to output an OCT beam, a laser source configured to output a laser beam, and a plurality of components configured to one or more of condition, scan, combine, and direct one or more of the OCT beam and the laser beam.

The control system is coupled to the second optical subsystem and is configured to instruct the OCT imaging apparatus to output an OCT beam and the laser source to output a laser beam, for delivery through the cornea, and the anterior chamber into the irido-corneal angle. The control system is also configured to instruct the laser source to modify a volume of ocular tissue within the outflow pathway to reduce a pathway resistance present in one or more of the trabecular meshwork, the Schlemm's canal, and the one or more collector channels by applying the laser beam to ocular tissue defining the volume to thereby cause photo-disruptive interaction with the ocular tissue to reduce the pathway resistance or create a new outflow pathway.

In one aspect of the system, the second optical subsystem is configured to direct the OCT beam and the laser beam toward the first optical subsystem. In a further aspect, the eye is characterized by a direction of view, the first optical subsystem by a first optical axis, and the first optical subsystem is adapted to be coupled to the eye so that the first optical axis is substantially aligned with the direction of view. The OCT beam and the laser beam are directed toward the first optical subsystem along a second optical axis offset from the first optical axis by an angle α. In an additional aspect, the exit lens has a convex surface and the OCT beam and the laser beam are directed into the convex surface of the exit lens at an angle β relative to a surface normal to the convex surface.

In further aspects, the control system is further configured to instruct the OCT imaging apparatus to acquire a diagnostic OCT image of a portion of the irido-corneal angle prior to ocular tissue modification. Based on this image, the control system determines the volume of ocular tissue to modify based on the OCT image. In a detailed aspect, the control system is configured to determine the volume of ocular tissue to modify by determining a density distribution of collector channels around at least a portion of the circumference of the Schlemm's canal, identifying a region of the Schlemm's canal having a density above a threshold criterion; and including the proximity of the identified region in the volume of ocular tissue to modify.

It is understood that other aspects of apparatuses and methods will become apparent to those skilled in the art from the following detailed description, wherein various aspects of apparatuses and methods are shown and described by way of illustration. As will be realized, these aspects may be implemented in other and different forms and its several details are capable of modification in various other respects. Accordingly, the drawings and detailed description are to be regarded as illustrative in nature and not as restrictive.

BRIEF DESCRIPTION OF THE DRAWINGS

Various aspects of systems, apparatuses, and methods will now be presented in the detailed description by way of example, and not by way of limitation, with reference to the accompanying drawings, wherein:

FIGS. 9a and 9b are schematic illustrations of the focusing objective of the integrated surgical system of FIG. 7 coupled to (FIG. 9a) and decoupled from (FIG. 9b) the patient interface of the integrated surgical system of FIG. 7.

DETAILED DESCRIPTION

Disclosed herein are systems, apparatuses, and methods for safely and effectively reducing intra-ocular pressure (IOP) in the eye to either treat or reduce the risk of glaucoma. The systems, apparatuses, and methods enable access to the irido-corneal angle of the eye and integrate laser surgery techniques with high resolution imaging to precisely diagnose, locate, and treat abnormal ocular tissue conditions within the irido-corneal angle that may be causing elevated IOP.

An integrated surgical system disclosed herein is configured to reduce intraocular pressure in an eye having a cornea, an anterior chamber, and an irido-corneal angle comprising an aqueous humor outflow pathway formed of a trabecular meshwork, a Schlemm's canal, and one or more collector channels branching from the Schlemm's canal. The integrated surgical system also includes a first optical subsystem and a second optical subsystem. The first optical subsystem includes a window configured to be coupled to the cornea and an exit lens configured to be coupled to the window. The second optical subsystem includes an optical coherence tomography (OCT) imaging apparatus configured to output an OCT beam, a laser source configured to output a laser beam, and a plurality of components, e.g., lenses and mirrors, configured to condition, combine, or direct the OCT beam and the laser beam toward the first optical subsystem.

The integrated surgical system also includes a control system coupled to the OCT imaging apparatus, the laser source, and the second optical subsystem. The controller is configured to instruct the OCT imaging apparatus to output an OCT beam and the laser source to output a laser beam, for delivery through the cornea, and the anterior chamber into the irido-corneal angle. In one configuration, the control system controls the second optical subsystem, so the OCT beam and the laser beam are directed into the first optical subsystem along a second optical axis that is offset from the first optical axis and that extends into the irido-corneal angle along an angled beam path 30.

Figure 2:
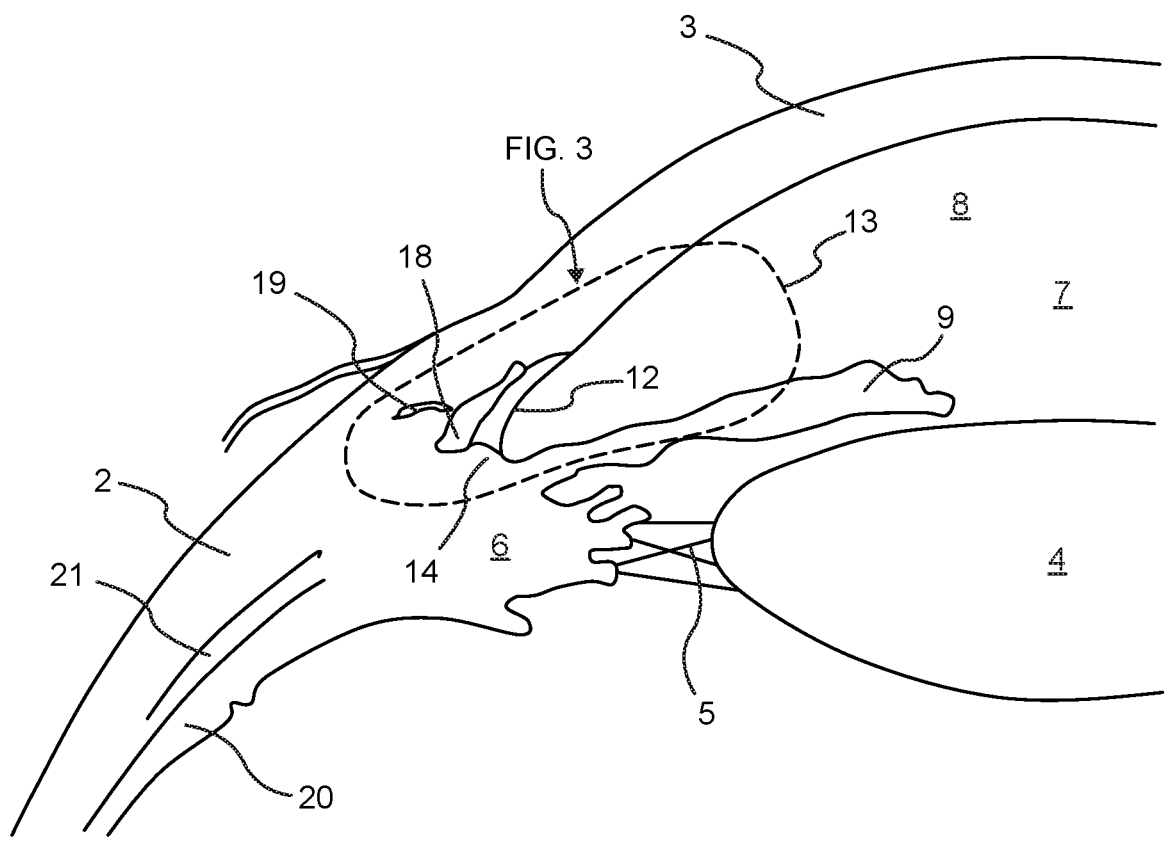
FIG. 2 is a sectional schematic illustration of the irido-corneal angle of the eye of FIG. 1.
Figure 3:
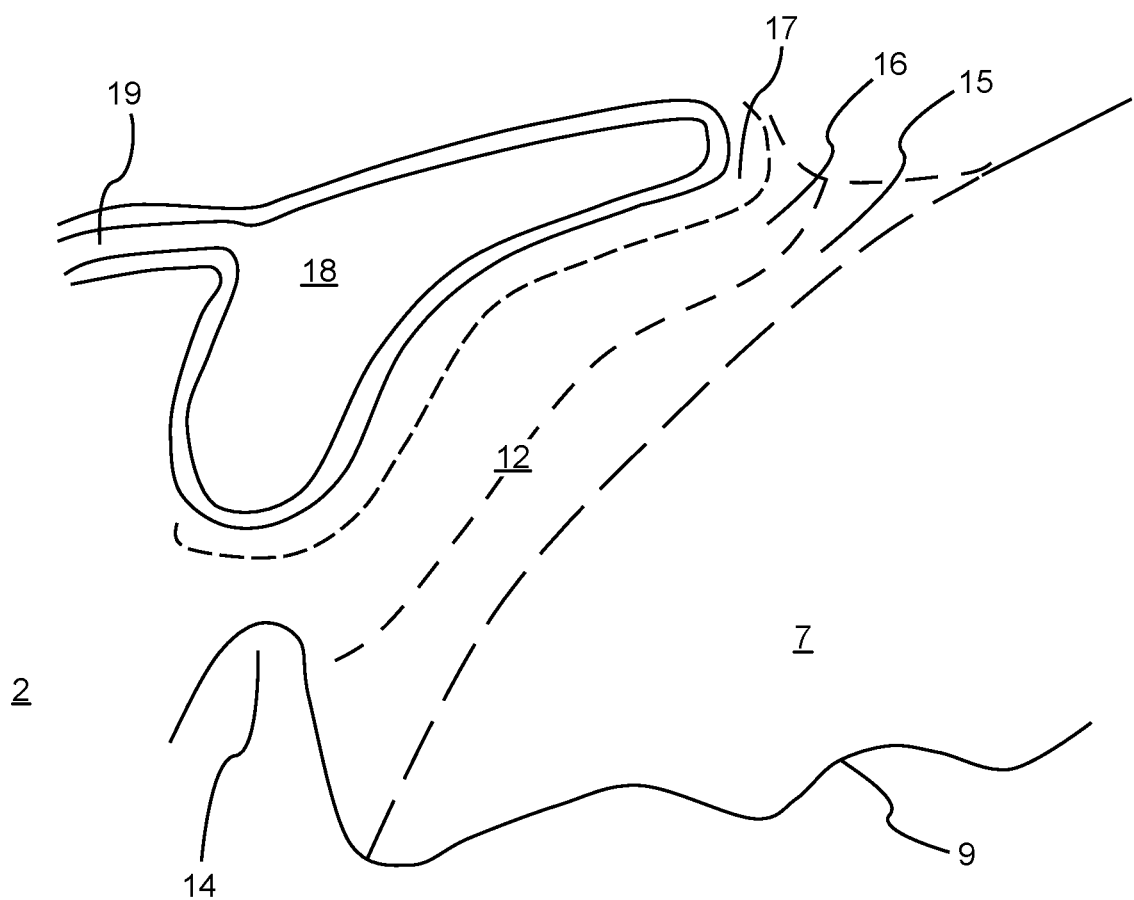
FIG. 3 is a sectional schematic illustration detailing anatomical structures in the irido-corneal angle of FIG. 2, including the trabecular meshwork, Schlemm's canal, and one or more collector channels branching from the Schlemm's canal.
Figure 4:
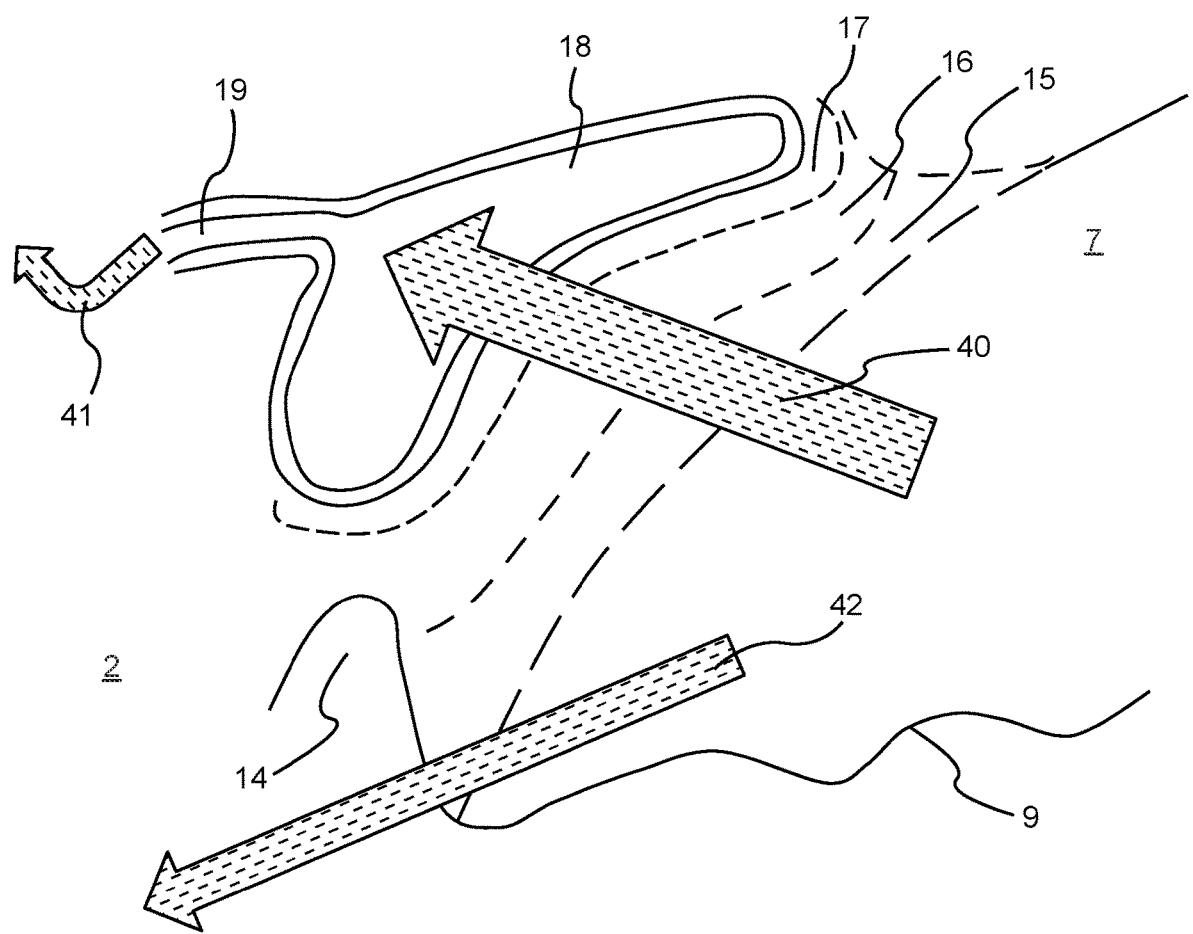
FIG. 4 is a sectional schematic illustration of various outflow pathways for aqueous humor through the trabecular meshwork, Schlemm's canal, and collector channels of FIG. 3.
Figure 5:
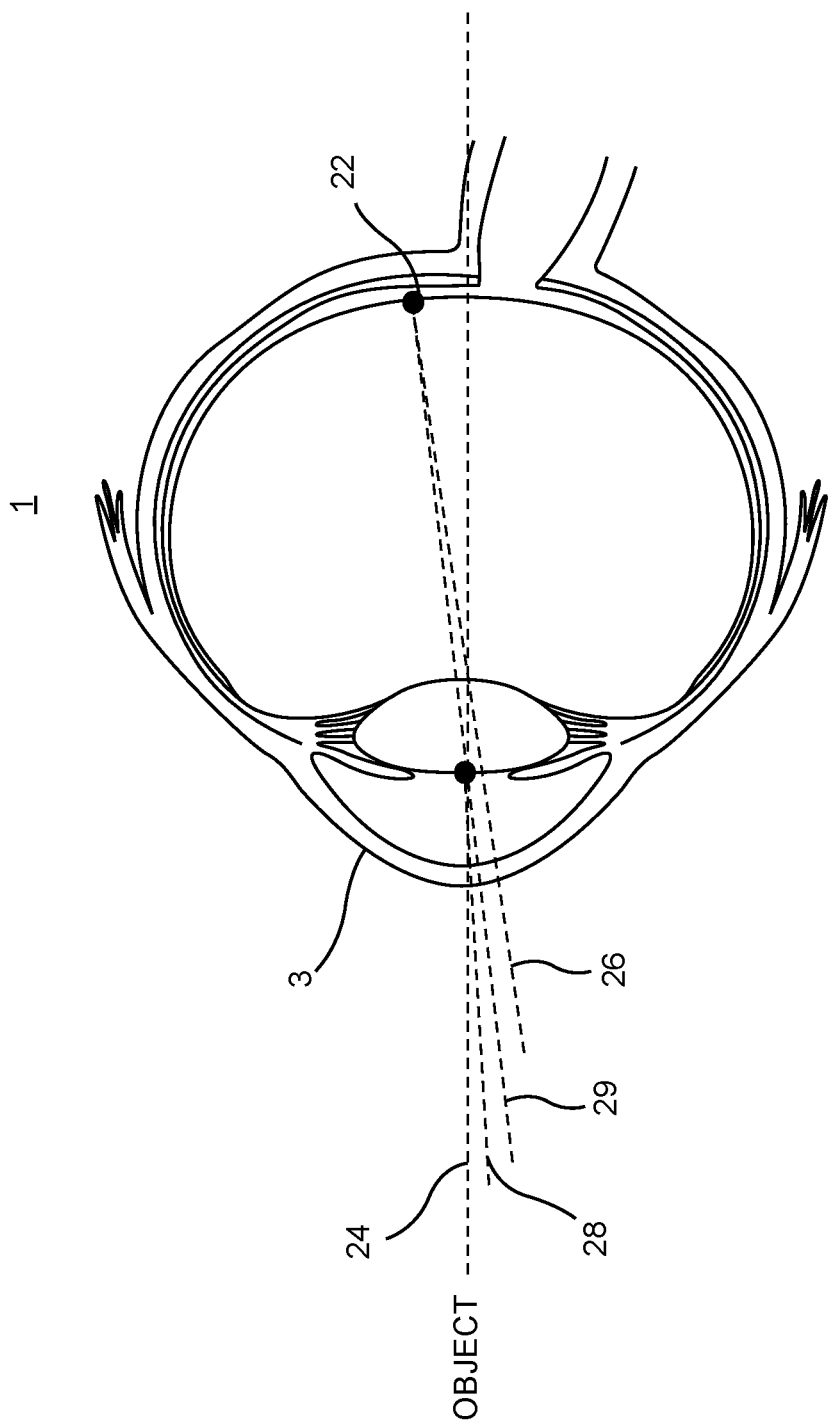
FIG. 5 is a sectional schematic illustration of a human eye showing various axes associated with the eye.

Directing each of an OCT beam and a laser beam along the same second optical axis into the irido-corneal angle of the eye is beneficial in that it enables direct application of the result of the evaluation of the condition into the treatment plan and surgery with precision in one clinical setting. Furthermore, combining OCT imaging and laser treatment allows targeting the ocular tissue with precision not available with any existing surgical systems and methods. Surgical precision afforded by the integrated surgical system allows for the affecting of only the targeted tissue of microscopic size and leaves the surrounding tissue intact. The microscopic size scale of the affected ocular tissue to be treated in the irido-corneal angle of the eye ranges from a few micrometers to a few hundred micrometers. For example, with reference to FIGS. 2 and 3, the cross-sectional size of the normal Schlemm's canal 18 is an oval shape of a few tens of micrometers by a few hundred micrometers. The diameter of collector channels 19 and veins is a few tens of micrometers. The thickness of the juxtacanalicular tissue 17 is a few micrometers, the thickness of the trabecular meshwork 12 is around a hundred micrometers.

The control system of the integrated surgical system is further configured to instruct the laser source to modify a volume of ocular tissue within the outflow pathway to reduce a pathway resistance present in one or more of the trabecular meshwork, the Schlemm's canal, and the one or more collector channels by applying the laser beam to ocular tissue defining the volume to thereby cause photo-disruptive interaction with the ocular tissue to reduce the pathway resistance or create a new outflow pathway.

The laser source may be a femtosecond laser. Femtosecond lasers provide non-thermal photo-disruption interaction with ocular tissue to avoid thermal damage to surrounding tissue. Further, unlike other surgical methods, with femtosecond laser treatment opening surface incisions penetrating the eye can be avoided, enabling a non-invasive treatment. Instead of performing the treatment in a sterile surgical room, the non-invasive treatment can be performed in a non-sterile outpatient facility.

An additional imaging component may be included the integrated surgical system to provide direct visual observation of the irido-corneal angle along an angle of visual observation. For example, a microscope or imaging camera may be included to assist the surgeon in the process of docking the eye to the patient interface or an immobilizing device, location of ocular tissues in the eye and observing the progress of the surgery. The angle of visual observation can also be along the angled beam path 30 to the irido-corneal angle 13 through the cornea 3 and the anterior chamber 7.

Images from the OCT imaging apparatus and the additional imaging component providing visual observation, e.g. microscope, are combined on a display device such as a computer monitor. Different images can be registered and overlaid on a single window, enhanced, processed, differentiated by false color for easier understanding. Certain features are computationally recognized by a computer processor, image recognition and segmentation algorithm can be enhanced, highlighted, marked for display. The geometry of the treatment plan can also be combined and registered with imaging information on the display device and marked up with geometrical, numerical and textual information. The same display can also be used for user input of numerical, textual and geometrical nature for selecting, highlighting and marking features, inputting location information for surgical targeting by keyboard, mouse, cursor, touchscreen, audio or other user interface devices.

OCT Imaging

Figure 1:
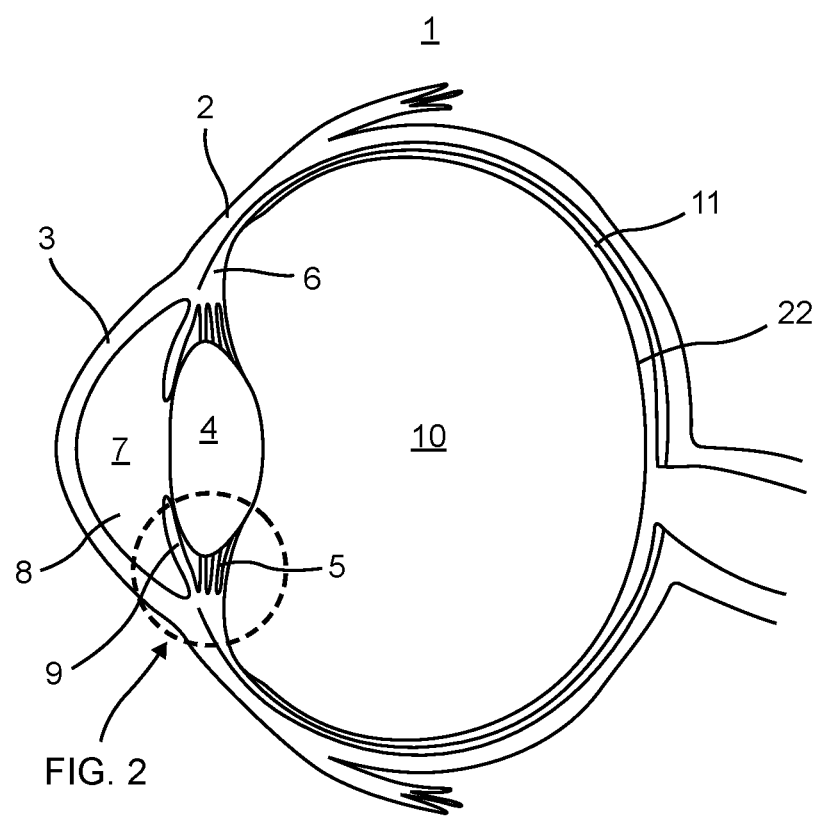
FIG. 1 is a sectional schematic illustration of a human eye and its interior anatomical structures.

The main imaging component of the integrated surgical system disclosed herein is an OCT imaging apparatus. OCT technology may be used to diagnose, locate and guide laser surgery directed to the irido-corneal angle of the eye. For example, with reference to FIGS. 1-3, OCT imaging may be used to determine the structural and geometrical conditions of the anterior chamber 7, to assess possible obstruction of the trabecular outflow pathway 40 and to determine the accessibility of the ocular tissue for treatment. As previously described, the iris 9 in a collapsed anterior chamber 7 may obstruct and close off the flow of aqueous humor 8, resulting in closed-angle glaucoma. In open-angle glaucoma, where the macroscopic geometry of the angle is normal, the permeability of ocular tissue may be affected, by blockage of tissue along the trabecular outflow pathway 40 or by the collapse of the Schlemm's canal 18 or collector channels 19.

OCT imaging can provide the necessary spatial resolution, tissue penetration and contrast to resolve microscopic details of ocular tissue. When scanned, OCT imaging can provide two-dimensional (2D) cross-sectional images of the ocular tissue. As another aspect of the integrated surgical system, 2D cross-sectional images may be processed and analyzed to determine the size, shape and location of structures in the eye for surgical targeting. It is also possible to reconstruct three-dimensional (3D) images from a multitude of 2D cross-sectional images but often it is not necessary. Acquiring, analyzing and displaying 2D images is faster and can still provide all information necessary for precise surgical targeting.

OCT is an imaging modality capable of providing high resolution images of materials and tissue. Imaging is based on reconstructing spatial information of the sample from spectral information of scattered light from within the sample. Spectral information is extracted by using an interferometric method to compare the spectrum of light entering the sample with the spectrum of light scattered from the sample. Spectral information along the direction that light is propagating within the sample is then converted to spatial information along the same axis via the Fourier transform. Information lateral to the OCT beam propagation is usually collected by scanning the beam laterally and repeated axial probing during the scan. 2D and 3D images of the samples can be acquired this way. Image acquisition is faster when the interferometer is not mechanically scanned in a time domain OCT, but interference from a broad spectrum of light is recorded simultaneously, this implementation is called a spectral domain OCT. Faster image acquisition may also be obtained by scanning the wavelength of light rapidly from a wavelength scanning laser in an arrangement called a swept-source OCT.

The axial spatial resolution limit of the OCT is inversely proportional to the bandwidth of the probing light used. Both spectral domain and swept source OCTs are capable of axial spatial resolution below 5 micrometers (µm) with sufficiently broad bandwidth of 100 nanometers (nm) or more. In the spectral domain OCT, the spectral interference pattern is recorded simultaneously on a multichannel detector, such as a charge coupled device (CCD) or complementary metal oxide semiconductor (CMOS) camera, while in the swept source OCT the interference pattern is recorded in sequential time steps with a fast optical detector and electronic digitizer. There is some acquisition speed advantage of the swept source OCT but both types of systems are evolving and improving rapidly, and resolution and speed is sufficient for purposes of the integrated surgical system disclosed herein. Stand-alone OCT systems and OEM components are now commercially available from multiple vendors, such as Optovue Inc., Fremont, Calif., Topcon Medical Systems, Oakland, N.J., Carl Zeiss Meditec AG, Germany, Nidek, Aichi, Japan, Thorlabs, Newton, N.J., Santec, Aichi, Japan, Axsun, Billercia, Mass., and other vendors.

Femtosecond Laser Source

The preferred surgical component of the integrated surgical system disclosed herein is a femtosecond laser. A femtosecond laser provides highly localized, non-thermal photo-disruptive laser-tissue interaction with minimal collateral damage to surrounding ocular tissue. Photo-disruptive interaction of the laser is utilized in optically transparent tissue. The principal mechanism of laser energy deposition into the ocular tissue is not by absorption but by a highly nonlinear multiphoton process. This process is effective only at the focus of the pulsed laser where the peak intensity is high. Regions where the beam is traversed but not at the focus are not affected by the laser. Therefore, the interaction region with the ocular tissue is highly localized both transversally and axially along the laser beam. The process can also be used in weakly absorbing or weakly scattering tissue. While femtosecond lasers with photo-disruptive interactions have been successfully used in ophthalmic surgical systems and commercialized in other ophthalmic laser procedures, none have been used in an integrated surgical system that accesses the irido-corneal angle.

In known refractive procedures, femtosecond lasers are used to create corneal flaps, pockets, tunnels, arcuate incisions, lenticule shaped incisions, partial or fully penetrating corneal incisions for keratoplasty. For cataract procedures the laser creates a circular cut on the capsular bag of the eye for capsulotomy and incisions of various patterns in the lens for braking up the interior of the crystalline lens to smaller fragments to facilitate extraction. Entry incisions through the cornea opens the eye for access with manual surgical devices and for insertions of phaco emulsification devices and intra-ocular lens insertion devices. Several companies have commercialized such surgical systems, among them the Intralase system now available from Jonhson & Johnson Vision, Santa Ana, Calif., The LenSx and Wavelight systems from Alcon, Fort Worth, Tex., other surgical systems from Bausch and Lomb, Rochester, N.Y., Carl Zeiss Meditec AG, Germany, Ziemer, Port, Switzerland, and LensAR, Orlando, Fla.

These existing systems are developed for their specific applications, for surgery in the cornea, and the crystalline lens and its capsular bag and are not capable of performing surgery in the irido-corneal angle 13 for several reasons. First, the irido-corneal angle 13 is not accessible with these surgical laser systems because the irido-corneal angle is too far out in the periphery and is outside of surgical range of these systems. Second, the angle of the laser beam from these systems, which is along the optical axis to the eye 24, is not appropriate to reaching the irido-corneal angle 13, where there is significant scattering and optical distortion at the applied wavelength. Third, any imaging capabilities these systems may have do not have the accessibility, penetration depth and resolution to image the tissue along the trabecular outflow pathway 40 with sufficient detail and contrast.

In accordance with the integrated surgical system disclosed herein, clear access to the irido-corneal angle 13 is provided along the angled beam path 30. The tissue, e.g., cornea 3 and the aqueous humor 8 in the anterior chamber 7, along this angled beam path 30 is transparent for wavelengths from approximately 400 nm to 2500 nm and femtosecond lasers operating in this region can be used. Such mode locked lasers work at their fundamental wavelength with Titanium, Neodymium or Ytterbium active material. Non-linear frequency conversion techniques known in the art, frequency doubling, tripling, sum and difference frequency mixing techniques, optical parametric conversion can convert the fundamental wavelength of these lasers to practically any wavelength in the above mentioned transparent wavelength range of the cornea.

Existing ophthalmic surgical systems apply lasers with pulse durations longer than 1 ns have higher photo-disruption threshold energy, require higher pulse energy and the dimension of the photo-disruptive interaction region is larger, resulting in loss of precision of the surgical treatment. When treating the irido-corneal angle 13, however, higher surgical precision is required. To this end, the integrated surgical system may be configured to apply lasers with pulse durations from 10 femtosecond (fs) to 1 nanosecond (ns) for generating photo-disruptive interaction of the laser beam with ocular tissue in the irido-corneal angle 13. While lasers with pulse durations shorter than 10 fs are available, such laser sources are more complex and more expensive. Lasers with the described desirable characteristics, e.g., pulse durations from 10 femtosecond (fs) to 1 nanosecond (ns), are commercially available from multiple vendors, such as Newport, Irvine, Calif., Coherent, Santa Clara, Calif., Amplitude Systems, Pessac, France, NKT Photonics, Birkerod, Denmark, and other vendors.

Accessing the Irido-Corneal Angle

Figure 6:
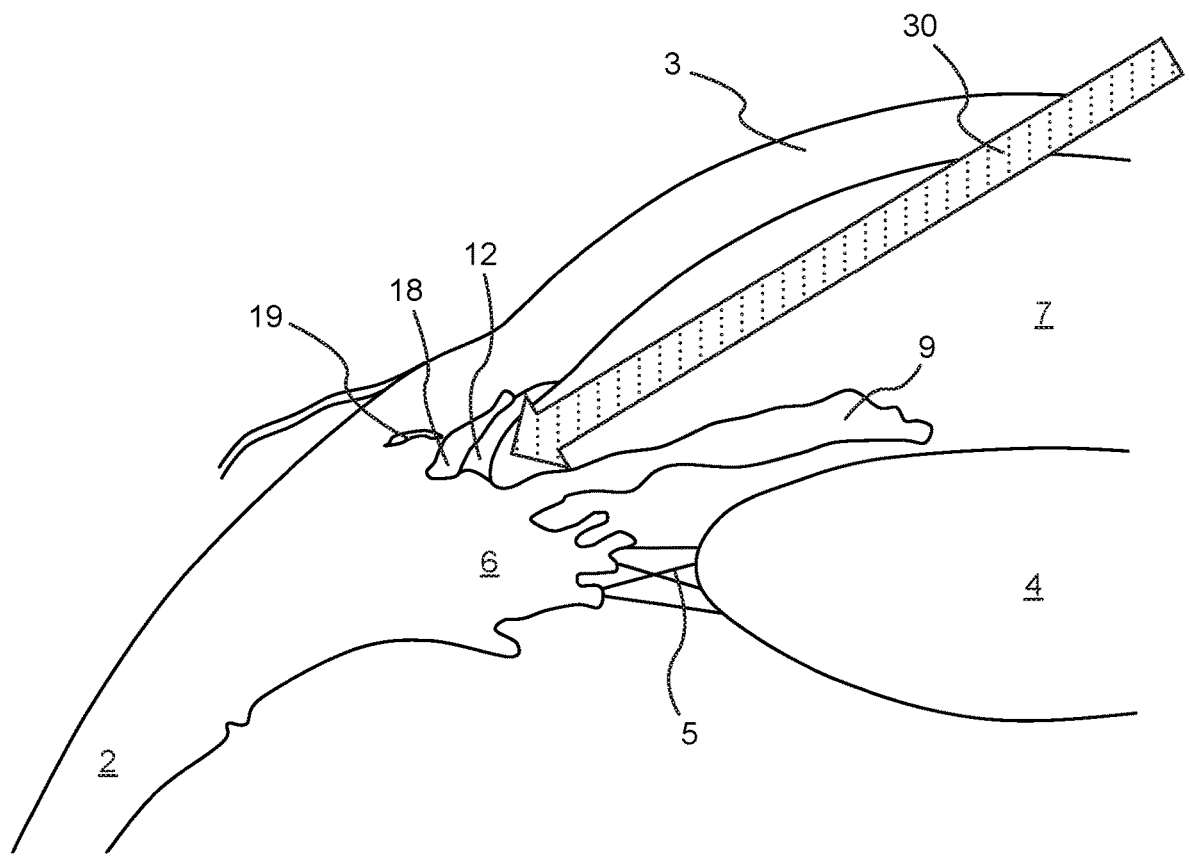
FIG. 6 is a sectional schematic illustration of an angled beam path along which one or more light beams may access the irido-corneal angle of the eye.

An important feature afforded by the integrated surgical system is access to the targeted ocular tissue in the irido-corneal angle 13. With reference to FIG. 6, the irido-corneal angle 13 of the eye may be accessed via the integrated surgical system along an angled beam path 30 passing through the cornea 3 and through the aqueous humor 8 in the anterior chamber 7. For example, one or more of an imaging beam, e.g., an OCT beam and/or a visual observation beam, and a laser beam may access the irido-corneal angle 13 of the eye along the angled beam path 30.

An optical system disclosed herein is configured to direct a light beam to an irido-corneal angle 13 of an eye along an angled beam path 30. The optical system includes a first optical subsystem and a second optical subsystem. The first optical subsystem includes a window formed of a material with a refractive index $n_w$ and has opposed concave and convex surfaces. The first optical subsystem also includes an exit lens formed of a material having a refractive index $n_x$. The exit lens also has opposed concave and convex surfaces. The concave surface of the exit lens is configured to couple to the convex surface of the window to define a first optical axis extending through the window and the exit lens. The concave surface of the window is configured to detachably couple to a cornea of the eye with a refractive index $n_c$ such that, when coupled to the eye, the first optical axis is generally aligned with the direction of view of the eye.

The second optical subsystem is configured to output a light beam, e.g., an OCT beam or a laser beam. The optical system is configured so that the light beam is directed to be incident at the convex surface of the exit lens along a second optical axis at an angle aα that is offset from the first optical axis. The respective geometries and respective refractive indices $n_x$, and $n_w$ of the exit lens and window are configured to compensate for refraction and distortion of the light beam by bending the light beam so that it is directed through the cornea 3 of the eye toward the irido-corneal angle 13. More specifically, the first optical system bends the light beam to that the light beam exits the first optical subsystem and enters the cornea 3 at an appropriate angle so that the light beam progresses through the cornea and the aqueous humor 8 in a direction along the angled beam path 30 toward the irido-corneal angle 13.

Accessing the irido-corneal angle 13 along the angled beam path 30 provides several advantages. An advantage of this angled beam path 30 to the irido-corneal angle 13 is that the OCT beam and laser beam passes through mostly clear tissue, e.g., the cornea 3 and the aqueous humor 8 in the anterior chamber 7. Thus, scattering of these beams by tissue is not significant. With respect to OCT imaging, this enables the use of shorter wavelength, less than approximately 1 micrometer, for the OCT to achieve higher spatial resolution. An additional advantage of the angled beam path 30 to the irido-corneal angle 13 through the cornea 3 and the anterior chamber 7 is the avoidance of direct laser beam or OCT beam light illuminating the retina 11. As a result, higher average power laser light and OCT light can be used for imaging and surgery, resulting in faster procedures and less tissue movement during the procedure.

Another important feature provided by the integrated surgical system is access to the targeted ocular tissue in the irido-corneal angle 13 in a way that reduces beam discontinuity. To this end, the window and exit lens components of the first optical subsystem are configured to reduce the discontinuity of the optical refractive index between the cornea 3 and the neighboring material and facilitate entering light through the cornea at a steep angle.

Having thus generally described the integrated surgical system and some of its features and advantages, a more detailed description of the system and its component parts follows.

Integrated Surgical System

Figure 7:
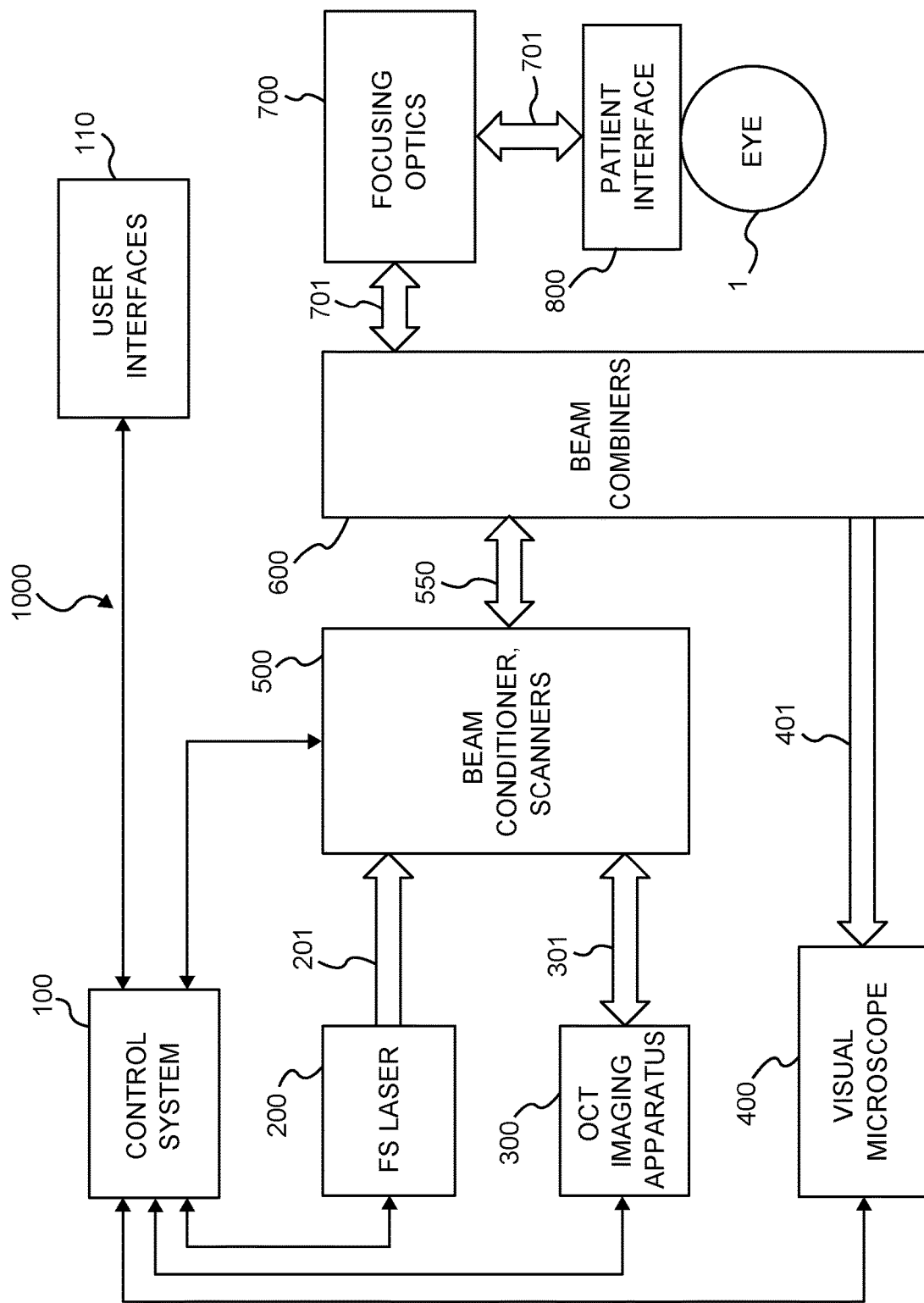
FIG. 7 is a block diagram of an integrated surgical system for non-invasive glaucoma surgery including a control system, a femtosecond laser source, an OCT imaging apparatus, a microscope, beam conditioners and scanners, beam combiners, a focusing objective, and a patient interface.

With reference to FIG. 7, an integrated surgical system 1000 for non-invasive glaucoma surgery includes a control system 100, a surgical component 200, a first imaging component 300 and an optional second imaging component 400. In the embodiment of FIG. 7, the surgical component 200 is a femtosecond laser source, the first imaging component 300 is an OCT imaging apparatus, and the optional second imaging component 400 is a visual observation apparatus, e.g., a microscope, for direct viewing or viewing with a camera. Other components of the integrated surgical system 1000 include beam conditioners and scanners 500, beam combiners 600, a focusing objective 700, and a patient interface 800.

The control system 100 may be a single computer or and plurality of interconnected computers configured to control the hardware and software components of the other components of the integrated surgical system 1000. A user interface 110 of the control system 100 accepts instructions from a user and displays information for observation by the user. Input information and commands from the user include but are not limited to system commands, motion controls for docking the patients eye to the system, selection of preprogrammed or live generated surgical plans, navigating through menu choices, setting of surgical parameters, responses to system messages, determining and acceptance of surgical plans and commands to execute the surgical plan. Outputs from the system towards the user includes but are not limited to display of system parameters and messages, display of images of the eye, graphical, numerical and textual display of the surgical plan and the progress of the surgery.

The control system 100 is connected to the other components 200, 300, 400, 500 of the integrated surgical system 1000. Control signals from the control system 100 to the femtosecond laser source 200 function to control internal and external operation parameters of the laser source, including for example, power, repetition rate and beam shutter. Control signals from the control system 100 to the OCT imaging apparatus 300 function to control OCT beam scanning parameters, and the acquiring, analyzing and displaying of OCT images.

Laser beams 201 from the femtosecond laser source 200 and OCT beams 301 from the OCT imaging apparatus 300 are directed towards a unit of beam conditioners and scanners 500. Different kind of scanners can be used for the purpose of scanning the laser beam 201 and the OCT beam 301. For scanning transversal to a beam 201, 301, angular scanning galvanometer scanners are available for example from Cambridge Technology, Bedford, Mass., Scanlab, Munich, Germany. To optimize scanning speed, the scanner mirrors are typically sized to the smallest size, which still support the required scanning angles and numerical apertures of the beams at the target locations. The ideal beam size at the scanners is typically different from the beam size of the laser beam 201 or the OCT beam 301, and different from what is needed at the entrance of a focusing objective 700. Therefore, beam conditioners are applied before, after or in between individual scanners. The beam conditioner and scanners 500 includes scanners for scanning the beam transversally and axially. Axial scanning changes the depth of the focus at the target region. Axial scanning can be performed by moving a lens axially in the beam path with a servo or stepper motor.

The laser beam 201 and the OCT beam 301 are combined with dichroic, polarization or other kind of beam combiners 600 to reach a common target volume or surgical volume in the eye. In an integrated surgical system 1000 having a femtosecond laser source 200, an OCT imaging apparatus 300, and a visual observation device 400, the individual beams 201, 301, 401 for each of these components may be individually optimized and may be collinear or non-collinear to one another. The beam combiner 600 uses dichroic or polarization beam splitters to split and recombine light with different wavelength and/or polarization. The beam combiner 600 may also include optics to change certain parameters of the individual beams 201, 301, 401 such as beam size, beam angle and divergence. Integrated visual illumination, observation or imaging devices assist the surgeon in docking the eye to the system and identifying surgical locations.

To resolve ocular tissue structures of the eye in sufficient detail, the imaging components 300, 400 of the integrated surgical system 1000 may provide an OCT beam and a visual observation beam having a spatial resolution of several micrometers. The resolution of the OCT beam is the spatial dimension of the smallest feature that can be recognized in the OCT image. It is determined mostly by the wavelength and the spectral bandwidth of the OCT source, the quality of the optics delivering the OCT beam to the target location in the eye, the numerical aperture of the OCT beam and the spatial resolution of the OCT imaging apparatus at the target location. In one embodiment, the OCT beam of the integrated surgical system has a resolution of no more than 5 µm.

Likewise, the surgical laser beam provided by the femtosecond laser source 200 may be delivered to targeted locations with several micrometer accuracy. The resolution of the laser beam is the spatial dimension of the smallest feature at the target location that can be modified by the laser beam without significantly affecting surrounding ocular tissue. It is determined mostly by the wavelength of the laser beam, the quality of the optics delivering the laser beam to target location in the eye, the numerical aperture of the laser beam, the energy of the laser pulses in the laser beam and the spatial resolution of the laser scanning system at the target location. In addition, to minimize the threshold energy of the laser for photo-disruptive interaction, the size of the laser spot should be no more than approximately 5 µm.

It should be noted that, while the visual observation beam 401 is acquired by the visual observation device 400 using fixed, non-scanning optics, the OCT beam 301 of the OCT imaging apparatus 300 is scanned laterally in two transversal directions. The laser beam 201 of the femtosecond laser source 200 is scanned in two lateral dimensions and the depth of the focus is scanned axially.

For practical embodiments, beam conditioning, scanning and combining the optical paths are certain functions performed on the laser, OCT and visual observation optical beams. Implementation of those functions may happen in a different order than what is indicated in FIG. 7. Specific optical hardware that manipulates the beams to implement those functions can have multiple arrangements with regards to how the optical hardware is arranged. They can be arranged in a way that they manipulate individual optical beams separately, in another embodiment one component may combine functions and manipulates different beams. For example, a single set of scanners can scan both the laser beam 201 and the OCT beam 301. In this case, separate beam conditioners set the beam parameters for the laser beam 201 and the OCT beam 301, then a beam combiner combines the two beams for a single set of scanners to scan the beams. While many combinations of optical hardware arrangements are possible for the integrated surgical system, the following section describes in detail an example arrangement.

Beam Delivery

In the following description, the term beam may—depending on the context—refer to one of a laser beam, an OCT beam, or a visual observation beam. A combined beam refers to two or more of a laser beam, an OCT beam, or a visual observation beam that are either collinearly combined or non-collinearly combined. Example combined beams include a combined OCT/laser beam, which is a collinear or non-colinear combination of an OCT beam and a laser beam, and a combined OCT/laser/visual beam, which is a collinear or non-collinear combination of an OCT beam, a laser beam, and a visual beam. In a collinearly combined beam, the different beams may be combined by dichroic or polarization beam splitters, and delivered along a same optical path through a multiplexed delivery of the different beams. In a non-collinear combined beam, the different beams are delivered at the same time along different optical paths that are separated spatially or by an angle between them. In the description to follow, any of the foregoing beams or combined beams may be generically referred to as a light beam. The terms distal and proximal may be used to designate the direction of travel of a beam, or the physical location of components relative to each other within the integrated surgical system. The distal direction refers to a direction toward the eye; thus an OCT beam output by the OCT imaging apparatus moves in the distal direction toward the eye. The proximal direction refers to a direction away from the eye; thus an OCT return beam from the eye moves in the proximal direction toward the OCT imaging apparatus.

Figure 8:
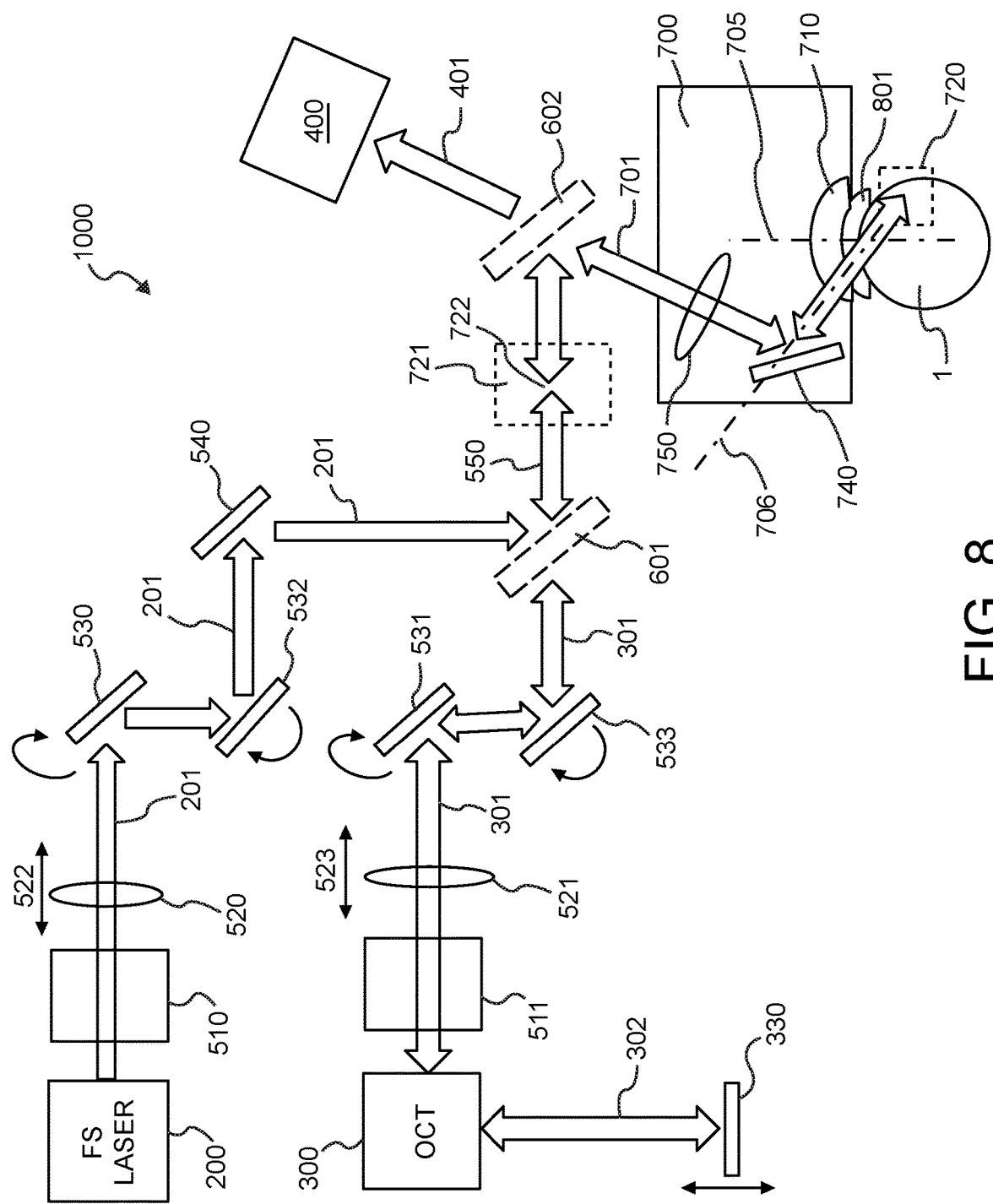
FIG. 8 is a detailed block diagram of the integrated surgical system of FIG. 7.

Referring to FIG. 8, an example integrated surgical system is configured to deliver each of a laser beam 201 and an OCT beam 301 in the distal direction toward an eye 1, and receive each of an OCT return beam and the visual observation beam 401 back from the eye 1. Regarding the delivery of a laser beam, a laser beam 201 output by the femtosecond laser source 200 passes through a beam conditioner 510 where the basic beam parameters, beam size, divergence are set. The beam conditioner 510 may also include additional functions, setting the beam power or pulse energy and shutter the beam to turn it on or off. After existing the beam conditioner 510, the laser beam 210 enters an axial scanning lens 520. The axial scanning lens 520, which may include a single lens or a group of lenses, is movable in the axial direction 522 by a servo motor, stepper motor or other control mechanism. Movement of the axial scanning lens 520 in the axial direction 522 changes the axial distance of the focus of the laser beam 210 at a focal point.

In accordance with a particular embodiment of the integrated surgical system, an intermediate focal point 722 is set to fall within, and is scannable in, the conjugate surgical volume 721, which is an image conjugate of the surgical volume 720, determined by the focusing objective 700. The surgical volume 720 is the spatial extent of the region of interest within the eye where imaging and surgery is performed. For glaucoma surgery, the surgical volume 720 is the vicinity of the irido-corneal angle 13 of the eye.

A pair of transverse scanning mirrors 530, 532 rotated by a galvanometer scanner scan the laser beam 201 in two essentially orthogonal transversal directions, e.g., in the x and y directions. Then the laser beam 201 is directed towards a dichroic or polarization beam splitter 540 where it is reflected toward a beam combining mirror 601 configured to combine the laser beam 201 with an OCT beam 301.

Regarding delivery of an OCT beam, an OCT beam 301 output by the OCT imaging apparatus 300 passes through a beam conditioner 511, an axially moveable focusing lens 521 and a transversal scanner with scanning mirrors 531 and 533. The focusing lens 521 is used set the focal position of the OCT beam in the conjugate surgical volume 721 and the real surgical volume 720. The focusing lens 521 is not scanned for obtaining an OCT axial scan. Axial spatial information of the OCT image is obtained by Fourier transforming the spectrum of the interferometrically recombined OCT return beam 301 and reference beams 302. However, the focusing lens 521 can be used to re-adjust the focus when the surgical volume 720 is divided into several axial segments. This way the optimal imaging spatial resolution of the OCT image can be extended beyond the Rayleigh range of the OCT signal beam, at the expense of time spent on scanning at multiple ranges.

Proceeding in the distal direction toward the eye 1, after the scanning mirrors 531 and 533, the OCT beam 301 is combined with the laser beam 201 by the beam combiner mirror 601. The OCT beam 301 and laser beam 201 components of the combined laser/OCT beam 550 are multiplexed and travel in the same direction to be focused at an intermediate focal point 722 within the conjugate surgical volume 721. After having been focused in the conjugate surgical volume 721, the combined laser/OCT beam 550 propagates to a second beam combining mirror 602 where it is combined with a visual observation beam 401 to form a combined laser/OCT/visual beam 701.

The combined laser/OCT/visual beam 701 traveling in the distal direction then passes through the focusing objective 700, and a window 801 of a patient interface, where the intermediate focal point 722 of the laser beam within the conjugate surgical volume 721 is re-imaged into a focal point in the surgical volume 720. The focusing objective 700 re-images the intermediate focal point 722, through the window 801 of a patient interface, into the ocular tissue within the surgical volume 720.

A scattered OCT return beam 301 from the ocular tissue travels in the proximal direction to return to the OCT imaging apparatus 300 along the same paths just described, in reverse order. The reference beam 302 of the OCT imaging apparatus 300, passes through a reference delay optical path and return to the OCT imaging apparatus from a moveable mirror 330. The reference beam 302 is combined interferometrically with the OCT return beam 301 on its return within the OCT imaging apparatus 300. The amount of delay in the reference delay optical path is adjustable by moving the moveable mirror 330 to equalize the optical paths of the OCT return beam 301 and the reference beam 302. For best axial OCT resolution, the OCT return beam 301 and the reference beam 302 are also dispersion compensated to equalize the group velocity dispersion within the two arms of the OCT interferometer.

When the combined laser/OCT/visual beam 701 is delivered through the cornea 3 and the anterior chamber 7, the combined beam passes through posterior and anterior surface of the cornea at a steep angle, far from normal incidence. These surfaces in the path of the combined laser/OCT/visual beam 701 create excessive astigmatism and coma aberrations that need to be compensated for.

Figure 9B:
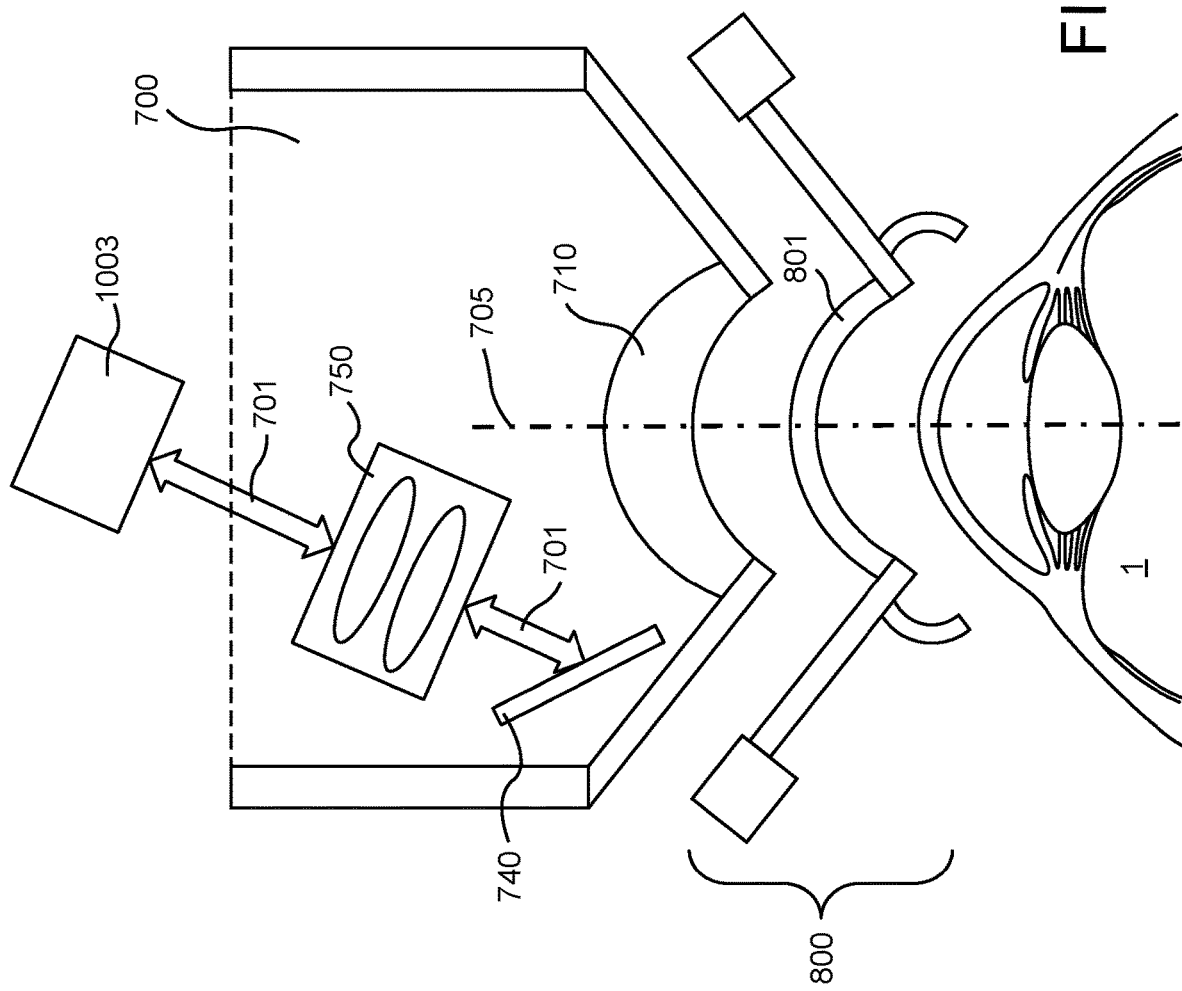

With reference to FIGS. 9a and 9b, in an embodiment of the integrated surgical system 1000, optical components of the focusing objective 700 and patient interface 800 are configured to minimize spatial and chromatic aberrations and spatial and chromatic distortions. FIG. 9a shows a configuration when both the eye 1, the patient interface 800 and the focusing objective 700 all coupled together. FIG. 9b shows a configuration when both the eye 1, the patient interface 800 and the focusing objective 700 all detached from one another.

The patient interface 800 optically and physically couples the eye 1 to the focusing objective 700, which in turn optically couples with other optic components of the integrated surgical system 1000. The patient interface 800 serves multiple functions. It immobilizes the eye relative to components of the integrated surgical system; creates a sterile barrier between the components and the patient; and provides optical access between the eye and the instrument. The patient interface 800 is a sterile, single use disposable device and it is coupled detachably to the eye 1 and to the focusing objective 700 of the integrated surgical system 1000.

Figure 9C:
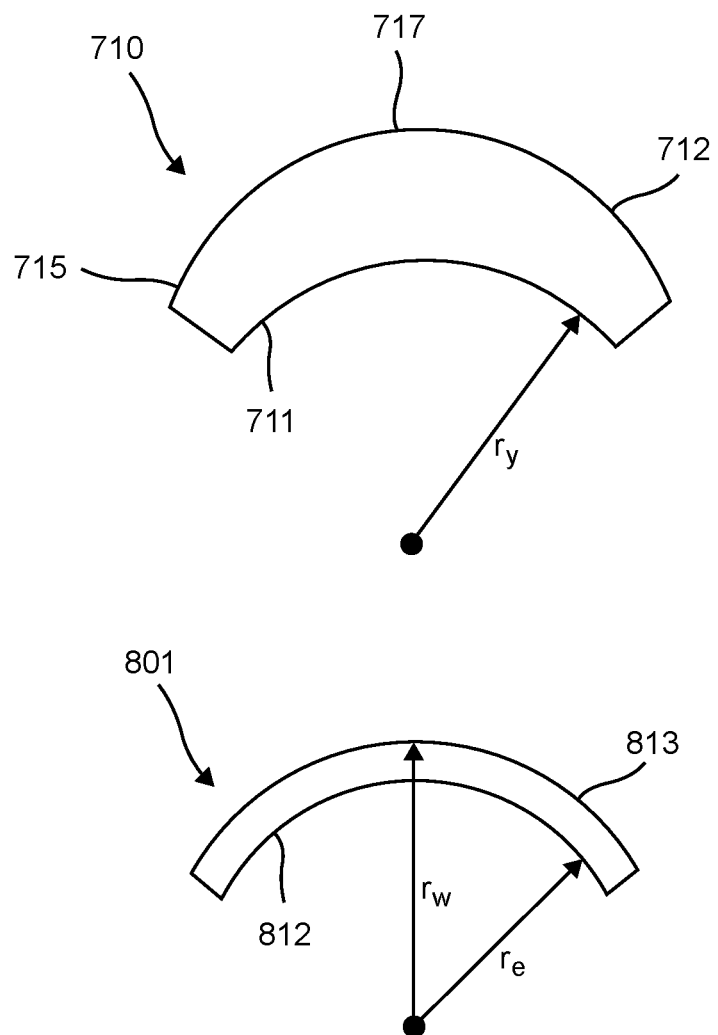
FIG. 9c is a schematic illustration of components of the focusing objective and the patient interface included in FIGS. 9a and 9b.

The patient interface 800 includes a window 801 having an eye-facing, concave surface 812 and an objective-facing, convex surface 813 opposite the concave surface. The window 801 thus has a meniscus form. With reference to FIG. 9c, the concave surface 812 is characterized by a radius of curvature $r_e$, while the convex surface 813 is characterized by a radius of curvature $r_w$. The concave surface 812 is configured to couple to the eye, either through a direct contact or through index matching material, liquid or gel, placed in between the concave surface 812 and the eye 1. The window 801 may be formed of glass and has a refractive index $n_w$. In one embodiment, the window 801 is formed of fused silica and has a refractive index $n_w$ of 1.45. Fused silica has the lowest index from common inexpensive glasses. Fluoropolymers such as the Teflon AF are another class of low index materials that have refractive indices lower than fused silica, but their optical quality is inferior to glasses and they are relatively expensive for high volume production. In another embodiment the window 801 is formed of the common glass BK7 and has a refractive index $n_w$ of 1.50. A radiation resistant version of this glass, BK7G18 from Schott AG, Mainz, Germany, allows gamma sterilization of the patient interface 800 without the gamma radiation altering the optical properties of the window 801.

Returning to FIGS. 9a and 9b, the window 801 is surrounded by a wall 803 of the patient interface 800 and an immobilization device, such as a suction ring 804. When the suction ring 804 is in contact with the eye 1, an annular cavity 805 is formed between the suction ring and the eye. When vacuum applied to the suction ring 804 and the cavity via a vacuum tube a vacuum pump (not shown in FIGS. 9a and 9b), vacuum forces between the eye and the suction ring attach the eye to the patient interface 800 during surgery. Removing the vacuum releases or detach the eye 1.

The end of the patient interface 800 opposite the eye 1 includes an attachment interface 806 configured to attach to the housing 702 of the focusing objective 700 to thereby affix the position of the eye relative to the other components of the integrated surgical system 1000. The attachment interface 806 can work with mechanical, vacuum, magnetic or other principles and it is also detachable from the integrated surgical system.

The focusing objective 700 includes an aspheric exit lens 710 having an eye-facing, concave surface 711 and a convex surface 712 opposite the concave surface. The exit lens 710 thus has a meniscus form. While the exit lens 710 shown in FIGS. 9a and 9b is an aspheric lens giving more design freedom, in other configurations the exit lens may be a spherical lens. Alternatively, constructing the exit lens 710 as a compound lens, as opposed to a singlet, allows more design freedom to optimize the optics while preserving the main characteristics of the optical system as presented here. With reference to FIG. 9c, the concave surface 711 is characterized by a radius of curvature $r_j$, while the convex surface 712 is characterized by an aspheric shape. The aspheric convex surface 712 in combination with the spherical concave surface 711 result in an exit lens 710 having varying thickness, with the outer perimeter edges 715 of the lens being thinner than the central, apex region 717 of the lens. The concave surface 711 is configured to couple to the convex surface 813 of the window 801. In one embodiment, the exit lens 710 is formed of fused silica and has a refractive index $n_x$ of 1.45.

Figure 10A:
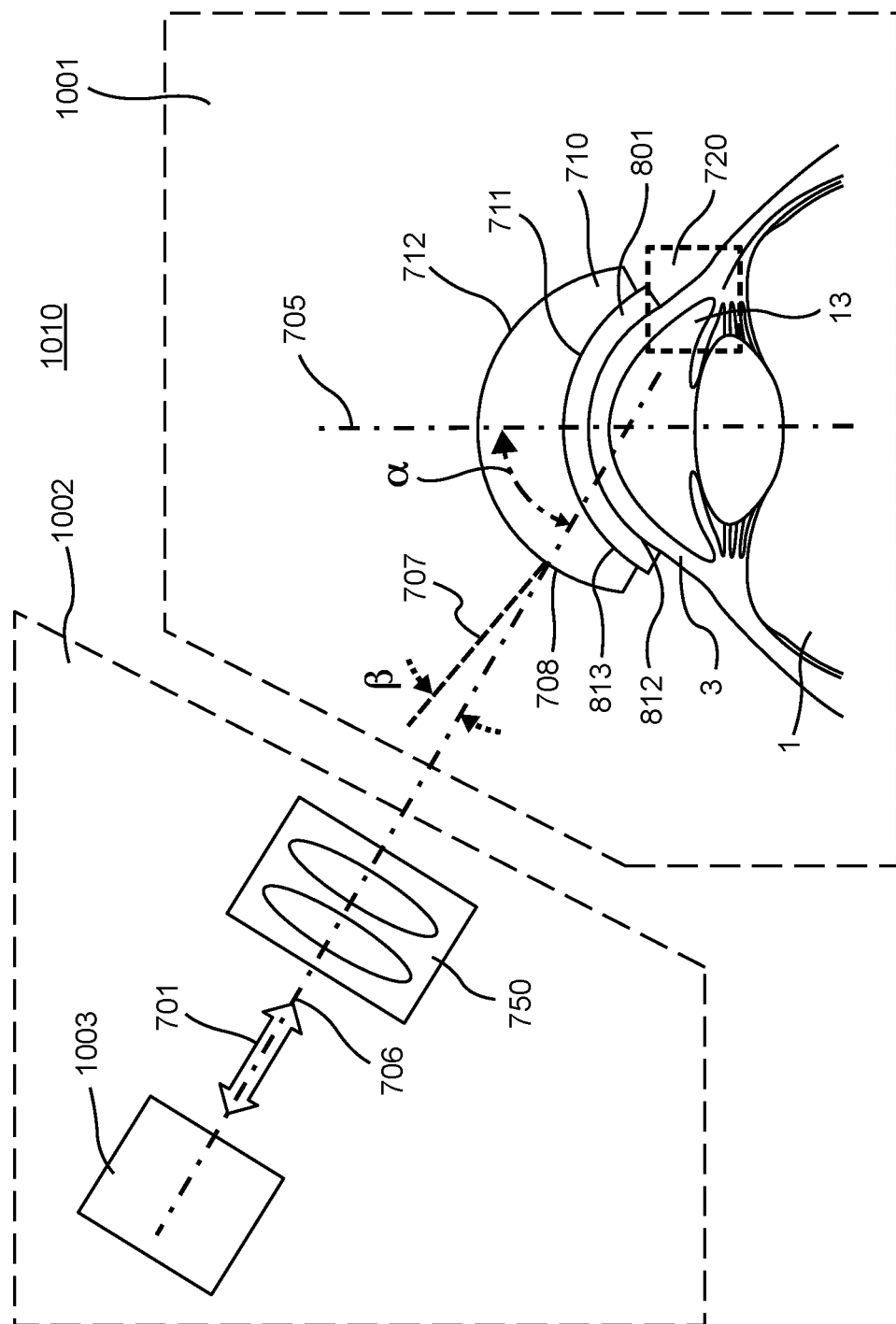
FIGS. 10a and 10b are schematic illustrations of components of the integrated surgical system of FIGS. 7 and 8 functionally arranged to form a first optical system and a second optical subsystem that enable access to the to the irido-corneal angle along the angled beam path of FIG. 6.
Figure 10B:
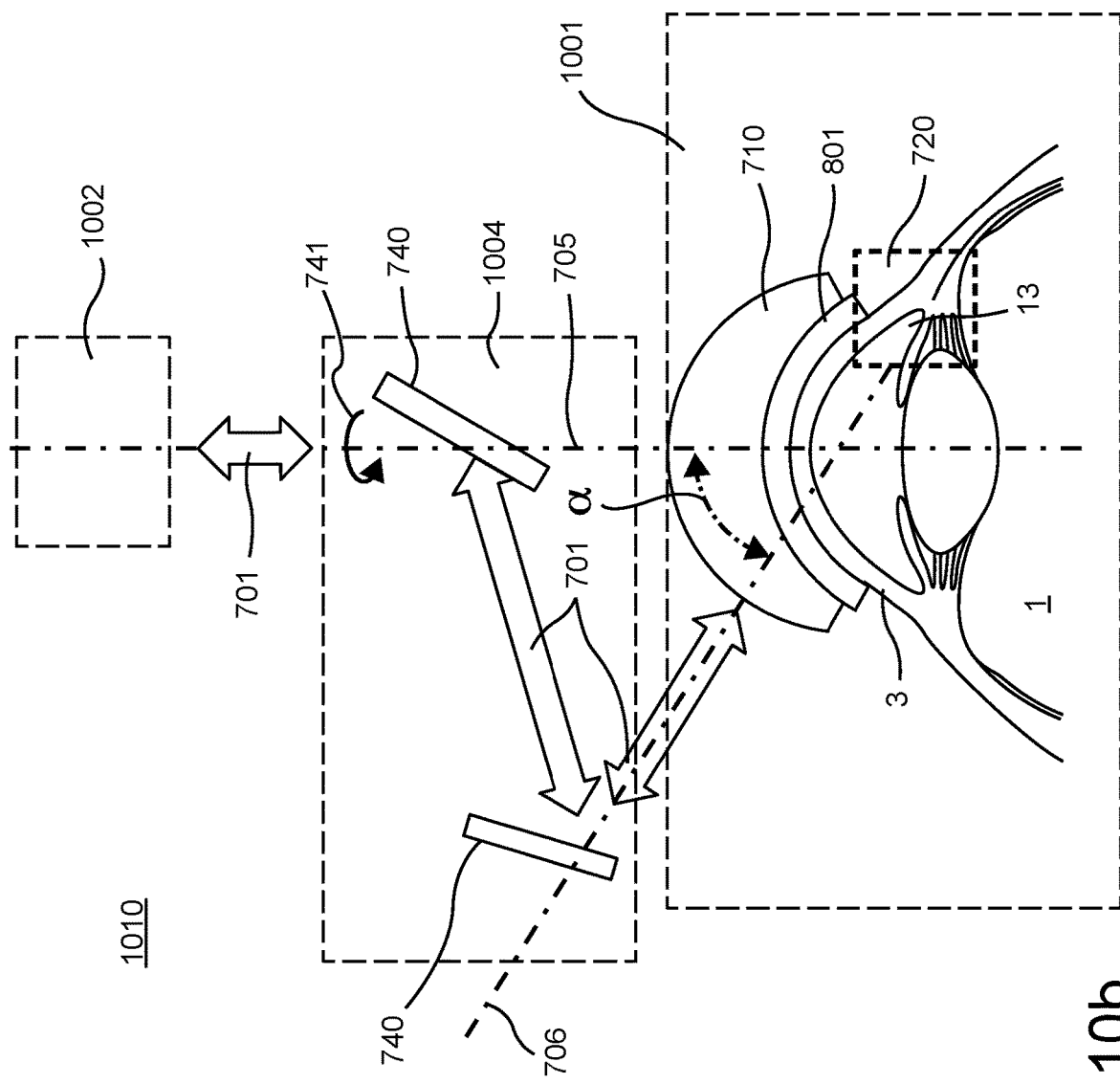
Figure 10C:
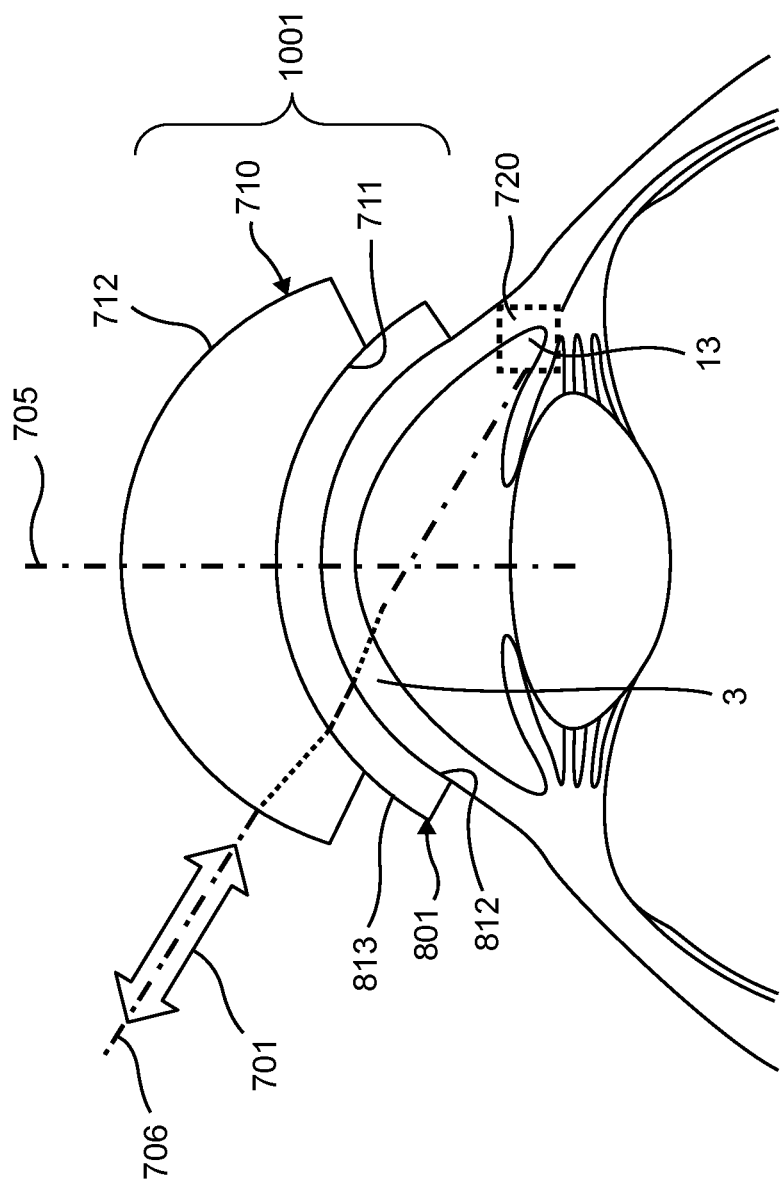
FIG. 10c is a schematic illustration of a beam passing through the first optical subsystem of FIGS. 10a and 10b and into the eye.

FIGS. 10a and 10b are schematic illustrations of components of the integrated surgical system of FIGS. 7 and 8 functionally arranged to form an optical system 1010 having a first optical subsystem 1001 and a second optical subsystem 1002 that enable access to a surgical volume 720 in the irido-corneal angle. Each of FIGS. 10a and 10b include components of the focusing objective 700 and the patient interface 800 of FIG. 9a. However, for simplicity, the entirety of the focusing objective and the patient interface are not included in FIGS. 10a and 10b. Also, for additional simplicity in FIG. 10a, the planar beam-folding mirror 740 of FIGS. 9a and 9b is not included and the combined laser/OCT/visual beam 701 shown in FIG. 9a is unfolded or straightened out. It is understood by those skilled in the art that adding or removing planar beam folding mirrors does not alter the principal working of the optical system formed by the first optical subsystem and the second optical subsystem. FIG. 10c is a schematic illustration of a beam passing through the first optical subsystem of FIGS. 10a and 10b.

With reference to FIG. 10a, a first optical subsystem 1001 of the integrated surgical system 1000 includes the exit lens 710 of a focusing objective 700 and the window 801 of a patient interface 800. The exit lens 710 and the window 801 are arranged relative to each other to define a first optical axis 705. The first optical subsystem 1001 is configured to receive a beam, e.g., a combined laser/OCT/visual beam 701, incident at the convex surface 712 of the exit lens 710 along a second optical axis 706, and to direct the beam toward a surgical volume 720 in the irido-corneal angle 13 of the eye.

During a surgical procedure, the first optical subsystem 1001 may be assembled by interfacing the convex surface 813 of the window 801 with the concave surface 711 of the exit lens 710. To this end, a focusing objective 700 is docked together with a patient interface 800. As a result, the concave surface 711 of the exit lens 710 is coupled to the convex surface 813 of the window 801. The coupling may be by direct contact or through a layer of index matching fluid. For example, when docking the patient interface 800 to focusing objective 700, a drop of index matching fluid can be applied between the contacting surfaces to eliminate any air gap that may be between the two surfaces 711, 813 to thereby help pass the combined laser/OCT/visual beam 701 through the gap with minimal Fresnel reflection and distortion.

In order to direct the beam toward the surgical volume 720 in the irido-corneal angle 13 of the eye, the first optical subsystem 1001 is designed to account for refraction of the beam 701 as it passes through the exit lens 710, the window 801 and the cornea 3. To this end, and with reference to FIG. 10c, the refractive index $n_x$ of the exit lens 710 and the refractive index $n_w$ of the window 801 are selected in view of the refractive index $n_c$ of the cornea 3 to cause appropriate beam bending through the first optical subsystem 1001 so that when the beam 701 exits the subsystem and passes through the cornea 3, the beam path is generally aligned to fall within the irido-corneal angle 13.

Continuing with reference to FIG. 10c and beginning with the interface between the window 801 and the cornea 3. Too steep of an angle of incidence at the interface where the combined laser/OCT/visual beam 701 exits the window 801 and enters the cornea 3, i.e., at the interface between the concave surface 812 of the window and the convex surface of the cornea 3, can create excessive refraction and distortion. To minimize refraction and distortion at this interface, in one embodiment of the first optical subsystem 1001, the refractive index of the window 801 is closely matched to the index of the cornea 3. For example, as describe above with reference to FIGS. 9a and 9b, the window 801 may have a refractive index lower than 1.42 to closely match the cornea 3, which has a refractive index of 1.36.

Excessive refraction and distortion at the interface where the combined laser/OCT/visual beam 701 exits the window 801 and enters the cornea 3 may be further compensated for by controlling the bending of the beam 701 as it passed through the exit lens 710 and the window 801. To this end, in one embodiment of the first optical subsystem 1001 the index of refraction $n_w$ of the window 801 is larger than each of the index of refraction $n_x$ of the exit lens 710 and the index of refraction $n_c$ of the cornea 3. As a result, at the interface where the combined laser/OCT/visual beam 701 exits the exit lens 710 and enters the window 801, i.e., interface between the concave surface 711 of the exit lens and the convex surface 813 of the window, the beam passes through a refractive index change from high to low that cause the beam to bend in a first direction. Then, at the interface where the combined laser/OCT/visual beam 701 exits the window 801 and enters the cornea 3, i.e., interface between the concave surface 812 of the exit lens and the convex surface of the cornea, the beam passes through a refractive index change from low to high that cause the beam to bend in a second direction opposite the first direction.

The shape of the window 801 is chosen to be a meniscus lens. As such, the incidence angle of light has similar values on both surfaces 812, 813 of the window 801. The overall effect is that at the convex surface 813 the light bends away from the surface normal and at the concave surface 812 the light bends towards the surface normal. The effect is like when light passes through a plan parallel plate. Refraction on one surface of the plate is compensated by refraction on the other surface a light passing through the plate does not change its direction. Refraction at the entering, convex surface 712 of the exit lens 710 distal to the eye is minimized by setting the curvature of the entering surface such that angle of incidence β of light 701 at the entering surface is close to a surface normal 707 to the entering surface at the intersection point 708.

Here, the exit lens 710, the window 801, and the eye 1 are arranged as an axially symmetric system with a first optical axis 705. In practice, axial symmetry is an approximation because of manufacturing and alignment inaccuracies of the optical components, the natural deviation from symmetry of the eye and the inaccuracy of the alignment of the eye relative to the window 801 and the exit lens 710 in a clinical setting. But, for design and practical purposes the eye 1, the window 801, and the exit lens 710 are considered as an axially symmetric first optical subsystem 1001.

With continued reference to FIG. 10a, a second optical subsystem 1002 is optically coupled to the first optical subsystem 1001 at an angle α relative to the first optical axis 705 of the first optical subsystem 1001. The advantage of this arrangement is that the both optical subsystems 1001, 1002 can be designed at a much lower numerical aperture compared to a system where all optical components are designed on axis with a common optical axis.

The second optical subsystem 1002 includes a relay lens 750 that, as previously described with reference to FIG. 8, generates a conjugate surgical volume 721 of the surgical volume 720 within the eye. The second optical subsystem 1002 includes various other components collectively indicated as an optical subsystem block 1003. Referring to FIG. 8, these components may include a femtosecond laser source 200, an OCT imaging apparatus 300, a visual observation device 400, beam conditioners and scanners 500, and beam combiners 600.

The second optical subsystem 1002 may include mechanical parts (not shown) configured to rotate the entire subsystem around the first optical axis 705 of the first optical subsystem 1001. This allows optical access to the whole 360-degree circumference of the irido-corneal angle 13 of the eye 1.

With reference to FIG. 10*b*, flexibility in arranging the first and second optical subsystems 1001, 1002, relative to each other may be provided by an optical assembly 1004 interposed between the optical output of the second optical subsystem 1002 and the optical input of the first optical subsystem 1001. In one embodiment, the optical assembly 1004 may include one or more planar beam-folding mirrors 740, prisms (not shown) or optical gratings (not shown) configured to receive the optical output, e.g., combined laser/OCT/visual beam 701, of the second optical subsystem 1002, change or adjust the direction of the combined laser/OCT/visual beam, and direct the beam to the optical input of the first optical subsystem 1001 while preserving the angle α between the first optical axis 705 and the second optical axis 706.

In another configuration, the optical assembly 1004 of planar beam-folding mirrors 740 further includes mechanical parts (not shown) configured to rotate the assembly around the first optical axis 705 of the first optical subsystem 1001 while keeping the second optical subsystem 1002 stationary. Accordingly, the second optical axis 706 of the second optical subsystem 1002 can be rotated around the first optical axis 705 of the first optical subsystem 1001. This allows optical access to the whole 360-degree circumference of the irido-corneal angle 13 of the eye 1.

With considerations described above with reference to FIGS. 9*a*, 9*b* and 9*c*, the design of the first optical subsystem 1001 is optimized for angled optical access at an angle α relative to the first optical axis 705 of the first optical subsystem 1001. Optical access at the angle α compensates for optical aberrations of the first optical subsystem 1001. Table 1 shows the result of the optimization at access angle α=72 degrees with Zemax optical design software package. This design is a practical embodiment for image guided femtosecond glaucoma surgery.

TABLE 1

| Surface | Structure and Material | Refractive index | Radius [mm] | Center Thickness [mm] |
| --- | --- | --- | --- | --- |
| concave surface 711, convex surface 712 | Exit lens 710 of focusing objective. Fused silica | 1.45 | −10 | 4.5 |
| concave surface 812, convex surface 813 | Window 801 of patient interface. BK7G18 | 1.50 | −10.9 | 1.0 |
| 3 | Cornea | 1.36 | −7.83 | 0.54 |
| 8 | Aqueous humor | 1.32 | −6.53 | 3.5 |
| Target | Ophthalmic tissue | 1.38 | N/A | 0 to 1 mm |

This design produces diffraction limited focusing of 1030 nm wavelength laser beams and 850 nm wavelength OCT beams with numerical aperture (NA) up to 0.2. In one design, the optical aberrations of the first optical subsystem are compensated to a degree that the Strehl ratio of the first optical subsystem for a beam with numerical aperture larger than 0.15 at the irido-corneal angle is larger than 0.9. In another design, the optical aberrations of the first optical subsystem are partially compensated, the remaining uncompensated aberrations of the first optical system are compensated by the second optical subsystem to a degree that the Strehl ratio of the combined first and second optical subsystem for a beam with numerical aperture larger than 0.15 at the irido-corneal angle is larger than 0.9.

Calibration

The femtosecond laser source 200, OCT imaging apparatus 300, and visual observation device 400 of the integrated surgical system 1000 are first individually calibrated to ensure their internal integrity and then cross-calibrated for system integrity. The essential part of system calibration is to ensure that the when the surgical focus of a laser beam 201 is commanded to a location of a surgical volume 720, as identified by the OCT imaging apparatus and/or the visual observation device 400, the achieved location of the focus matches the commanded location of the focus within a certain tolerance, typically within 5 to 10 μm. Also, graphical and cursor outputs, images, overlays displayed on a user interface 110, such as a computer monitor, and user inputs of ocular tissue surgical volume 720 locations accepted from the user interface 110 should correspond to actual locations in tissue within predetermined tolerances of similar accuracy.

One embodiment of this spatial calibration procedure starts with imaging calibrated scales and scaling magnifications of the OCT imaging apparatus 300 and/or the visual observation device 400 and their displays in a way that the scale value on the display matches the real scale of the calibration target. Then laser calibration patters are exposed or burned into transparent calibration targets, and the calibration patterns are subsequently imaged. Then, the intended patterns and the actual burned patterns are compared with the imaging system of the integrated surgical system 1000 or by a separate microscope. If they do not match within the specified tolerance, the scaling parameters of the surgical patterns are re-scaled by adjusting the scaling of the laser beam scanners. This procedure is iterated, if necessary, until all spatial calibrations are within tolerance.

Laser Surgery with Ocular Tissue Modification

The anatomy of the eye relevant to the surgical treatment enabled by the integrated surgical system 1000 disclosed herein is illustrated in FIGS. 1-4. To reduce the IOP, laser treatment targets ocular tissues that affect the trabecular outflow pathway 40. These ocular tissues may include the trabecular meshwork 12, the scleral spur 14, the uveal 15, the corneoscleral meshwork 16, the juxtacanalicular tissue 17, the Schlemm's canal 18, the collector channels 19 within the irido-corneal angle 13.

Disclosed herein is a laser pattern particularly effective in affecting the trabecular outflow pathway 40. Since the laser interaction volume is small, on the order of a few micrometers (μm), the interaction of ocular tissue with each laser shot of a repetitive laser breaks down ocular tissue locally at the focus of the laser. Pulse duration of the laser for photo-disruptive interaction in ocular tissue can range from several femtoseconds to several nanoseconds and pulse energies from several nanojoules to tens of microjoules. The laser pulses at the focus, through multiphoton processes, breaks down chemical bonds in the molecules, locally photo-dissociate tissue material and create gas bubbles in wet tissue. The breakdown of tissue material and mechanical stress from bubble formation fragments the tissue and create clean continuous cuts when the laser pulses are laid down in proximity to one another along geometrical lines and surfaces.

For the sake of the following description the basic interaction volumes are referred to as cells. The size of a cell is determined by the extent of the influence of the laser-tissue interaction. When the laser spots, or cells, are spaced close along a line, the laser creates a narrow, microscopic channel. A wider channel can be created by closely spacing a multitude of laser spots within the cross section of the channel. For example, a cylindrical channel can be created by first calculating the coordinates of the overall position and size of the cylinder. Then, using the size of the cells as a parameter, calculate the coordinates of each cell in a closely packed cell arrangement within the volume of the cylinder. The arrangement of the cells resembles the arrangement of atoms in a crystal structure.

The easiest is to calculate a cubic cell structure, in this case the individual cells are arranged in regularly spaced rows, columns and sheets, and the coordinates of the cells can be calculated sequentially from neighbor to neighbor in the order of rows columns and sheets. The laser scanner hardware can also follow this regular sequence to scan the laser beam without excessive jumps. Channels can be created with different cross sections, with oval, rectangular, square or other regular or irregular cross sections. A channel cut in the ocular tissue can conduct aqueous humor 8, its conductivity increasing with the cross-sectional area of the channel.

Figure 11A:
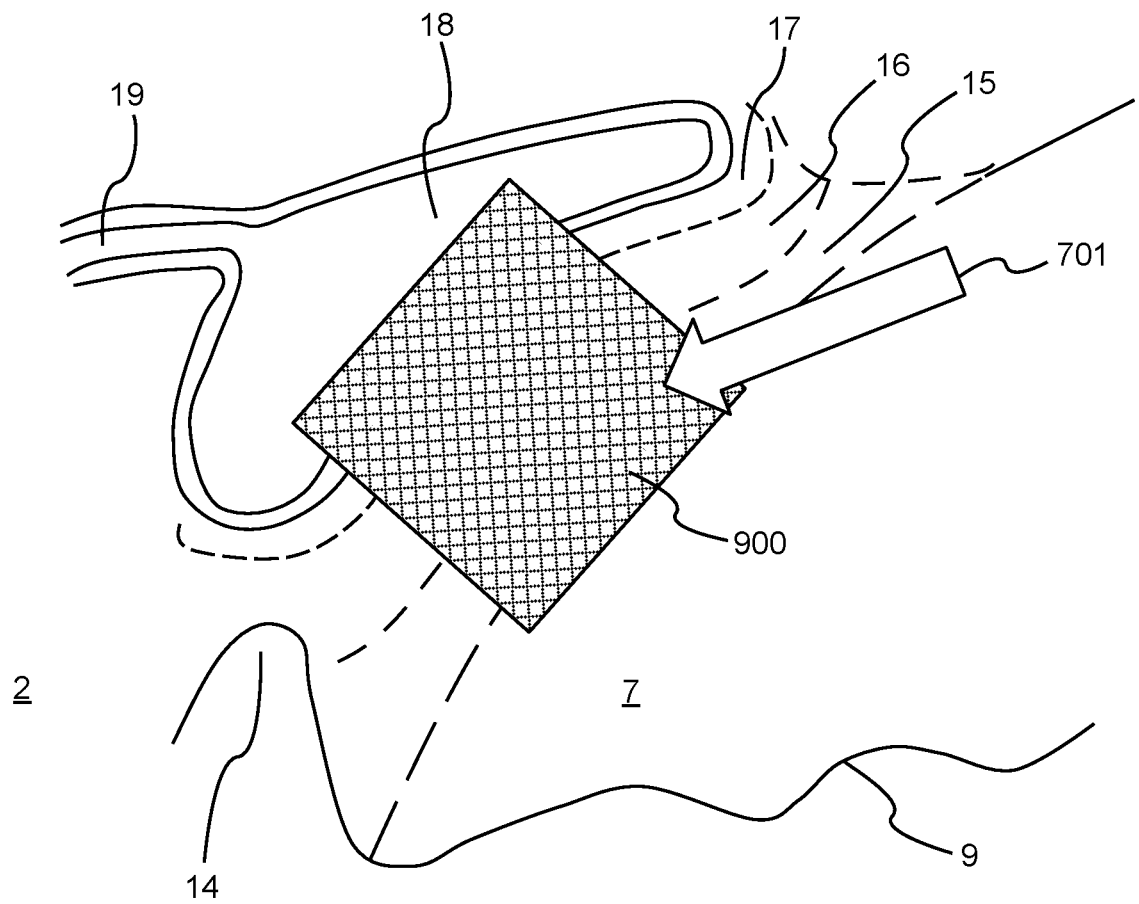
FIGS. 11a and 11b are schematic illustrations of a surgical volume (FIG. 11a) determined by the integrated surgical system of FIG. 7. and an outflow pathway (FIG. 11b) formed at the surgical volume by the integrated surgical system.
Figure 11B:
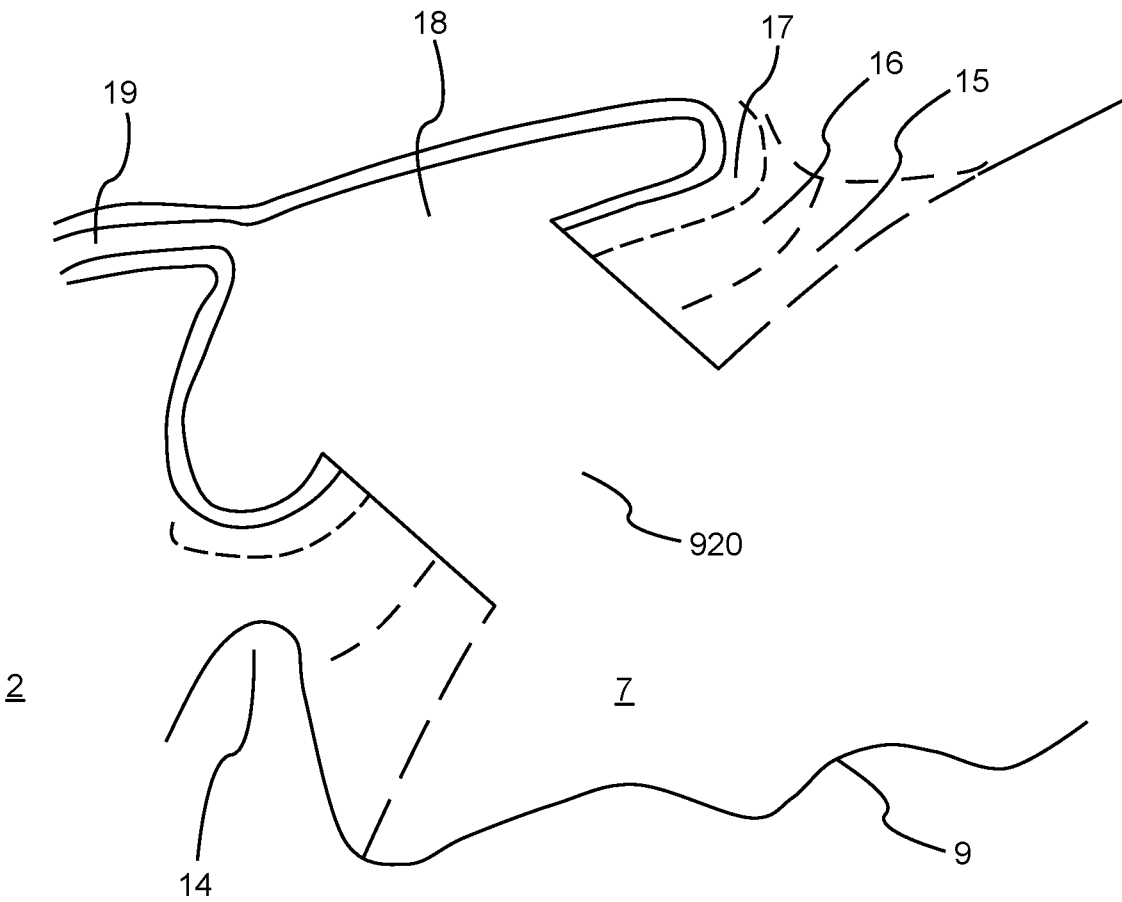

FIGS. 11a and 11b illustrate sectional views of the iridocorneal angle where the surgical laser scans to affect a surgical volume 900 (FIG. 11a) to form a channel opening 920 (FIG. 11b). The surgical volume 900 in the trabecular meshwork, extends from the anterior chamber 7 and through the inner wall of the Schlemm's canal 18. Laser scanning modifies the ocular tissue in the surgical volume 900 to create a channel opening 920. The channel opening 920 reduces the flow resistance in the ocular tissue to increase aqueous flow from the anterior chamber 7 into the Schlemm's canal 18 and thereby reduce the IOP of the eye. The size of the channel opening 920 will determine the reduction of the outflow path resistance and the longevity of effectiveness.

Image guidance is essential for this procedure to locate the structures precisely and to monitor the success of the treatment. Minimizing the size and volume of the treated ocular tissue also helps minimize the amount of gas created and gas-induced tissue movements. As the tissue expands with the expanding gas, sudden tissue movements can occur when gas escapes from a closed volume and the gas filled void collapses. Such sudden tissue movements can create discontinuities in the surgical incisions and should be avoided or minimized.

Another consideration for creating surgical patterns in the ocular tissue is the potential shadow effect of the gas bubbles as the incision progresses. In general, the incision progresses should proceed from a location further from the laser and progress towards a location closer to the laser to minimize the shadow effect. The amount of gas is also less when the laser is focused tightly to a diffraction limited focal spot and the threshold pulse energy for photo-disruption interaction is lowered. When the laser is operated at low threshold, the size of local interaction volume and the size of the gas bubbles are smaller. This means that the cells filling the surgical volume should be spaced closer.

Table 2 displays surgical laser and treatment pattern parameters for several incisions of different sizes. The range of the parameter set is limited by the Maximum Permissible Exposure (MPE) limit of laser light entering the eye and practical ranges for the repetition rate of the laser and the scanning speed of the scanners.

TABLE 2

| Tissue treated | Channel size x[mm], y[mm], z[mm] | Channel cross section [mm$^2$] | Cell size x[μm], y[μm], z[μm] | Laser average power [W] | Laser repetition rate [kHz] | Laser pulse energy [μJ] | Procedure time [s] |
| --- | --- | --- | --- | --- | --- | --- | --- |
| Trabecular meshwork | 1.5, 0.2, 0.2 | 0.3 | 3, 3, 3 | 0.9 | 300 | 3 | 7.4 |
| Trabecular meshwork | 2, 0.2, 0.2 | 0.4 | 4, 4, 4 | 1 | 200 | 5 | 6.3 |

With respect to MPE, the angled beam path 30 of FIG. 6 is the most advantageous since light beams from the femtosecond laser source 200 or the OCT imaging apparatus 300 transmitted through the tissue do not reach directly the retina. This is in contrast with known corneal and cataract surgeries, where direct laser light or OCT light transmitted through the tissue reaches the retina. Therefore, the angled beam path 30 of FIG. 6 can use higher beam average power. Higher average power for the surgical laser results in faster procedure time. Higher average power for the OCT beam results in faster OCT image acquisition time for the same image quality or better image quality for the same image acquisition time. With respect to cell size and laser pulse energy, smaller cell sizes and pulse energies are preferred to minimize the amount of gas created in the tissue.

Linear perfusion models, experimental (Liu et al., 2005) and clinical findings from ELT procedures indicate channel cross sections from 0.24 mm$^2$ to 0.4 mm$^2$ can achieve sufficient IOP reduction. As seen from Table 2, the surgical laser procedure enabled by the integrated surgical system disclosed herein can produce similar channel cross sections to those in Liu et al. and can be completed in less than 10 seconds.

Figure 12:
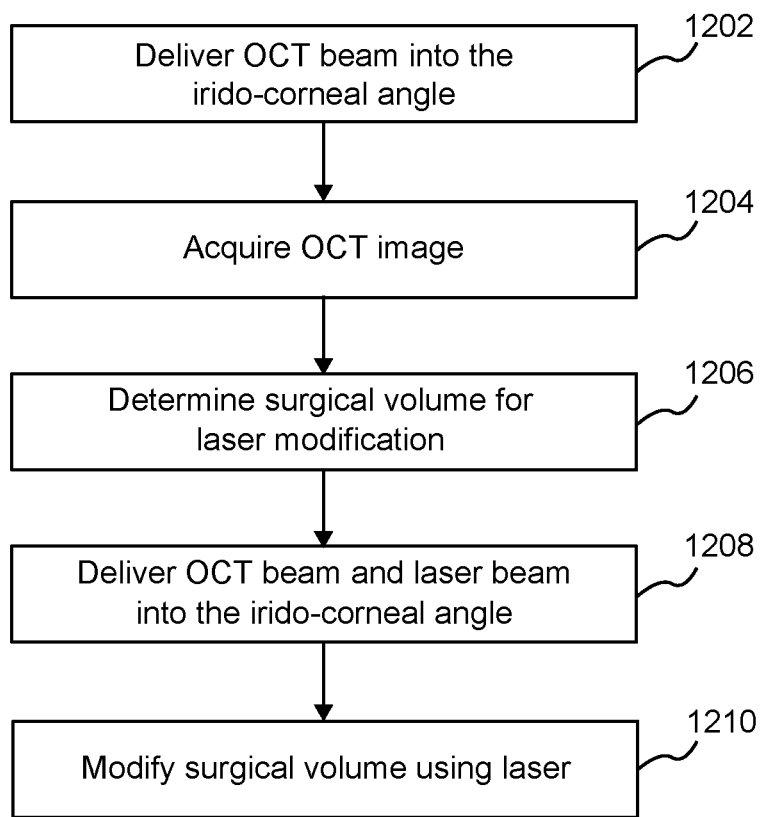
FIG. 12 is a flowchart of a method of modifying ocular tissue at the irido-corneal angle of the eye.

FIG. 12 is a flowchart of a method of reducing intraocular pressure in an eye having a cornea, an anterior chamber, and an irido-corneal angle comprising an aqueous humor outflow pathway formed of a trabecular meshwork, a Schlemm's canal, and one or more collector channels branching from the Schlemm's canal, the method comprising. The method may be performed by the integrated surgical system 1000 of FIGS. 7-10b.

At step 1202, an OCT beam 301 is delivered through the cornea 3 and the anterior chamber 7 into the irido-corneal angle 13. In one embodiment, the OCT beam 301 has a resolution less than or equal to approximately 5 micrometers and is delivered to the irido-corneal angle 13 by directing the OCT beam to a first optical subsystem 1001 that includes a window 801 coupled to the cornea 3 and an exit lens 710 coupled to the window.

At step 1204, an OCT image of a portion of the irido-corneal angle 13 is acquired based on the OCT beam 301 delivered to the irido-corneal angle through the first optical subsystem 1001. To this end, an OCT return beam 301 is received through the first optical subsystem 1001 and processed at an OCT imaging apparatus 300 using known OCT imaging techniques.

At step 1206, a surgical volume 900 of ocular tissue to be modified is determined based on the OCT image. The surgical volume 900 may be determined based on a 2D cross-sectional OCT image that is displayed on a control system 100 of the integrated surgical system 1000. A visual observation beam 401 may also be used to determine the surgical volume 900. To this end, a visual observation beam 401 may be acquired from the irido-corneal angle 13 by a microscope 400 through the first optical subsystem 1001, and the volume 900 of ocular tissue to modify may be determined by presenting the OCT image and visual observation signal overlaid on a display screen of the control system 100. Alternatively, the OCT image and visual observation signal may be registered on a display screen.

In one embodiment, the Schlemm's canal 18 is characterized by a circumference, and the surgical volume 900 of ocular tissue to modify is determined based on the density of collector channels 19 around the circumference. In this case, a density distribution of collector channels 19 around at least a portion of the circumference of the Schlemm's canal 18 is determined based on OCT images. A region of the Schlemm's canal 18 having a density above a threshold criterion is identified, and the proximity of the identified region is included in the volume of ocular tissue to modify. The criterion may be the $50^{th}$ percentile of the distribution, the $75^{th}$ percentile, or a numerical value higher than the $75^{th}$ percentile. In another embodiment, the volume 900 of ocular tissue to be modified is in the proximity of one or more of the collector channels 19.

At step 1208, each of an OCT beam 301 and a laser beam 201 is delivered through the cornea 3, and the anterior chamber 7 into the irido-corneal angle 13. In one embodiment, the OCT beam 301 and laser beam 201 have substantially equal resolutions, e.g., less than or equal to approximately 5 micrometers, and each beam is delivered to the irido-corneal angle by directing each beam to a first optical subsystem 1001 that includes a window 801 coupled to the cornea 3 and an exit lens 710 coupled to the window. The OCT beam 301 and the laser beam 201 may be collinearly directed to the first optical subsystem 1001 along a same optical path, for example by multiplexing the beams. Alternatively, the OCT beam 301 and the laser beam 201 may be non-collinearly directed to the first optical subsystem at the same time along spatially separated or angled optical paths.

Distortion and aberrations of the beams 201, 301 caused by oblique angle entry into the eye are compensated for by directing each beam into the first optical subsystem 1001 at an angle. To this end, the eye 1 includes a direction of view and the first optical subsystem 1001 is positioned relative to the eye so as to include a first optical axis 705 that is substantially aligned with the direction of view of the eye. The beams 201, 301 are input to the first optical subsystem 1001 by directing each beam into a convex surface 713 of the exit lens 710 along a second optical axis 706 offset from the first optical axis 705 by an angle α. Additionally, each beam 201, 301 may be directed into the convex surface 713 of the exit lens 710 at an angle β relative to a surface normal 707 to the convex surface.

At step 1210, a volume 900 of ocular tissue within the trabecular outflow pathway 40 is modified to reduce a pathway resistance present in one or more of the trabecular meshwork 12, the Schlemm's canal 18, and the one or more collector channels 19 by applying the laser beam 201 to ocular tissue defining the volume. To this end, a laser beam 201 having a wavelength between 330 nanometers and 2000 nanometers may be scanned in multiple directions to interact with the ocular tissue defining the surgical volume 900. The laser beam 201 may be applied in a continuous manner or as a multitude of laser pulses with a pulse duration between 20 femtoseconds and 1 nanosecond. The laser beam 201 causes photo-disruptive interaction with the ocular tissue to reduce the pathway resistance or create a new outflow pathway 40. In one embodiment, photo-disruptive interaction with the ocular tissue creates a channel 902 opened through the trabecular meshwork connecting the anterior chamber and the Schlemm's canal.

Accessing the Irido-Corneal Angle

Figure 13:
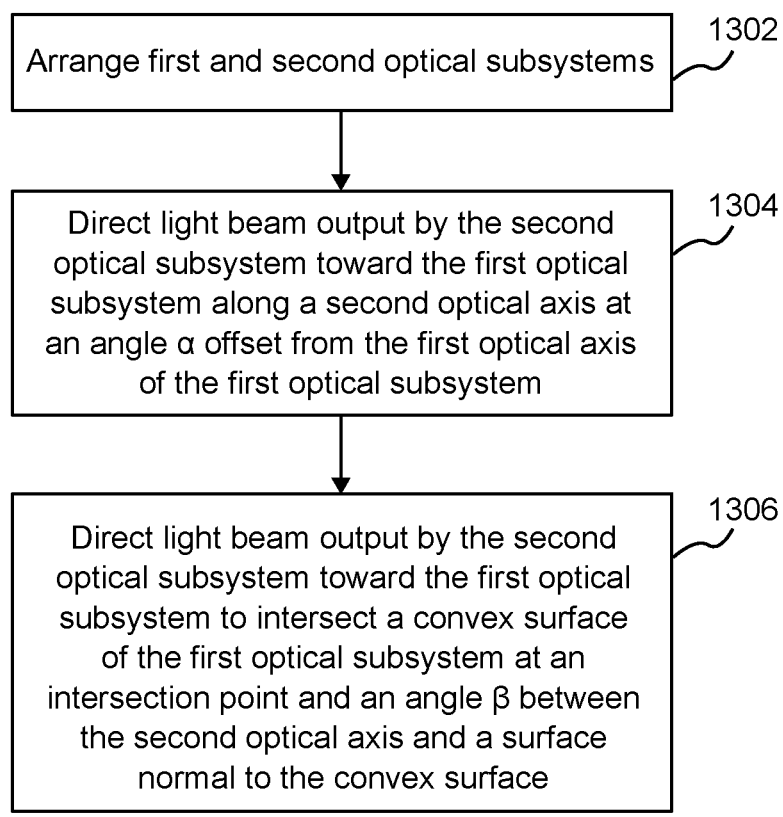
FIG. 13 is a flowchart of a method of delivering light beams to the irido-corneal angle of the eye along the angled beam path of FIG. 6.

FIG. 13 is a flowchart of a method of directing a light beam to an irido-corneal angle of an eye having a direction of view and a cornea with a refractive index $n_c$. The method may be performed by the integrated surgical system 1000 of FIGS. 7-10b.

At step 1302, a first optical subsystem 1001 and a second optical subsystem 1002 are arranged relative to each other. The first optical subsystem 1001 includes a window 801 formed of a material with a refractive index $n_w$. The window 801 has a concave surface 812 and a convex surface 813 opposite the concave surface. The first optical subsystem 1001 also includes and an exit lens 710 formed of a material having a refractive index $n_x$. The exit lens 710 has a concave surface 711 and a convex surface 712 opposite the concave surface. The concave surface 711 of the exit lens 710 is configured to couple to the convex surface 813 of the window 801 to define a first optical axis 705 extending through the window and the exit lens. The concave surface 812 of the window 801 is configured to detachably couple to the cornea 3 of the eye such that the first optical axis 705 is generally aligned with the direction of view of the eye.

At step 1304, a light beam output by the second optical subsystem 1002 is directed to be incident at the convex surface 712 of the exit lens 710 along a second optical axis 706 at an angle α that is offset from the first optical axis 705. To this end, the second optical subsystem 1002 or another intermediate optical assembly 1004 may be configured to determine a measure of angle separation between the first optical axis and the second optical axis, and to adjust the orientation of the second optical axis until the angle of separation is at angle α. The angle α is typically greater than 30 degrees. More specifically, the angle α may be between 60 degrees and 80 degrees. Even more specifically, the angle α is approximately 72 degrees.

At step 1306, the light beam output by the second optical subsystem 1002 may be also directed to intersect the convex surface 712 of the exit lens 710 at an intersection point and an angle β between the second optical axis 706 and a surface normal 707 to the convex surface of the exit lens. Again, the second optical subsystem 1002 or another intermediate optical assembly 1004 may be configured to determine a measure of angle separation between the second optical axis and the surface normal 707, and to adjust the orientation of the second optical axis until the angle of separation is at angle β.

In some arrangements, as shown for example in FIG. 10b, the second optical subsystem 1002 may be configured to be arrange relative to the first optical subsystem 1001 so that the light beam 701 is output by the second optical subsystem along an axis offset from the second optical axis 706. In these cases, in the directing process of block 1304, the light beam 701 is received at an optical assembly 1004 interposed between the first optical subsystem 1001 and the second optical subsystem 1002 and redirected into general alignment with the second optical axis 706. The second optical axis 706 may be rotated around the first optical axis 705 while maintaining the second optical axis offset from the first optical axis by an angle substantially equal to the angle α. Doing so allows for treatment around the circumference of the irido-corneal angle 13. In configurations where the second optical axis 706 intersects the convex surface 712 of the exit lens 710 at an intersection point 708 and at an angle β between the second optical axis and a surface normal 707 to the convex surface of the exit lens, the directing process of block 1306 involves rotating the second optical axis around the first optical axis while also maintaining an angle between the second optical axis and the surface normal that is substantially equal to the angle β.

The various aspects of this disclosure are provided to enable one of ordinary skill in the art to practice the present invention. Various modifications to exemplary embodiments presented throughout this disclosure will be readily apparent to those skilled in the art. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

It is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method of reducing intraocular pressure in an eye having a direction of view, a cornea, an anterior chamber, and an irido-corneal angle comprising an aqueous humor outflow pathway formed of a trabecular meshwork, a Schlemm's canal, and one or more collector channels branching from the Schlemm's canal, the method comprising:

simultaneously delivering each of an optical coherence tomography (OCT) beam and a laser beam to a first optical subsystem along a same angled beam path that extends through the first optical subsystem and through the cornea and the anterior chamber into the irido-corneal angle, the first optical subsystem comprising a window adapted to be coupled to the cornea and an exit lens coupled to the window, and a first optical axis substantially aligned with the direction of view, wherein simultaneously delivering each of the OCT beam and the laser beam to the first optical subsystem comprises collinearly combining the OCT beam and the laser beam by components of a second optical subsystem configured to rotate about the first optical axis independent of corresponding movement of the exit lens, and directing the collinearly combined beam into the first optical subsystem along a second optical axis offset from the first optical axis by an angle α;

modifying a volume of ocular tissue within the aqueous humor outflow pathway to reduce a pathway resistance present in one or more of the trabecular meshwork, the Schlemm's canal, and the one or more collector channels by applying the laser beam to ocular tissue defining the volume to thereby cause photo-disruptive interaction with the ocular tissue to reduce the pathway resistance or create a new outflow pathway;

rotating the second optical subsystem about the first optical axis without rotating the exit lens;

simultaneously delivering each of the OCT beam and the laser beam to the first optical subsystem along a same angled beam path; and modifying an additional volume of ocular tissue within the aqueous humor outflow pathway.

2. The method of claim 1, wherein the exit lens comprises a convex surface and directing the collinearly combined beam into the first optical subsystem further comprises directing the collinearly combined beam into the convex surface of the exit lens at an angle β relative to a surface normal to the convex surface.

3. The method of claim 1, wherein applying the laser beam comprises scanning the laser beam to interact with the ocular tissue defining the volume.

4. The method of claim 1, wherein photo-disruptive interaction with the ocular tissue creates a channel opened through the trabecular meshwork connecting the anterior chamber and the Schlemm's canal.

5. The method of claim 1, wherein the wavelength of the laser beam is between 330 nanometers and 2000 nanometers.

6. The method of claim 1, wherein the laser beam is composed of a multitude of laser pulses with pulse duration between 20 femtoseconds and 1 nanosecond.

7. The method of claim 1, wherein the volume of ocular tissue is in a proximity of one or more of the collector channels.

8. The method of claim 1, wherein the laser beam and the OCT beam have respective resolutions that are substantially equal.

9. The method of claim 8, wherein the respective resolutions are less than or equal to approximately 5 micrometers.

10. The method of claim 1, further comprising, prior to simultaneously delivering each of an OCT beam and a laser beam:

delivering an OCT beam to the first optical subsystem and through the cornea and the anterior chamber into the irido-corneal angle;

acquiring an OCT image of a portion of the irido-corneal angle; and determining the volume of ocular tissue to modify based on the OCT image.

11. The method of claim 10, wherein the OCT image comprises a two-dimensional cross-sectional image.

12. The method of claim 10, wherein determining the volume of ocular tissue to modify comprises presenting the OCT image on a display screen.

13. The method of claim 10, wherein the Schlemm's canal is characterized by a circumference, and determining the volume of ocular tissue to modify comprises:

determining a density distribution of collector channels around at least a portion of the circumference of the Schlemm's canal;

identifying a region of the Schlemm's canal having a density above a threshold criterion; and including a proximity of the identified region in the volume of ocular tissue to modify.

14. The method of claim 10, further comprising acquiring a visual observation signal from the irido-corneal angle.

15. The method of claim 14, wherein determining the volume of ocular tissue to modify comprises presenting the OCT image and visual observation signal overlaid on a display screen.

16. The method of claim 14, wherein determining the volume of ocular tissue to modify comprises presenting the OCT image and visual observation signal registered on a display screen.

17. A method of reducing intraocular pressure in an eye having a direction of view, a cornea, an anterior chamber, and an irido-corneal angle comprising an aqueous humor outflow pathway formed of a trabecular meshwork, a Schlemm's canal, and one or more collector channels branching from the Schlemm's canal, the method comprising:

simultaneously delivering each of an optical coherence tomography (OCT) beam and a laser beam to a first optical subsystem along a same angled beam path that extends through the first optical subsystem and through the cornea and the anterior chamber into the irido-corneal angle, the first optical subsystem comprising a window adapted to be coupled to the cornea and an exit lens coupled to the window, and a first optical axis substantially aligned with the direction of view, wherein simultaneously delivering each of the OCT beam and the laser beam to the first optical subsystem comprises collinearly combining the OCT beam and the laser beam and directing the collinearly combined beam into the first optical subsystem along a second optical axis offset from the first optical axis by an angle a, and wherein the OCT beam and the laser beam are collinearly combined by components of a second optical subsystem and the collinearly combined beam is input to the first optical subsystem through an optical assembly coupled between the first optical subsystem and the second optical subsystem and configured to rotate about the first optical axis independent of corresponding movement of the exit lens and the second optical subsystem modifying a volume of ocular tissue within the aqueous humor outflow pathway to reduce a pathway resistance present in one or more of the trabecular meshwork, the Schlemm's canal, and the one or more collector channels by applying the laser beam to ocular tissue defining the volume to thereby cause photo-disruptive interaction with the ocular tissue to reduce the pathway resistance or create a new outflow pathway;

rotating the optical assembly about the first optical axis without rotating the exit lens and the second optical subsystem;

simultaneously delivering each of the OCT beam and the laser beam to the first optical subsystem along a same angled beam path; and modifying an additional volume of ocular tissue within the aqueous humor outflow pathway.

18. The method of claim 17, wherein the optical assembly comprises one or more beam folding mirrors.

19. The method of claim 17, wherein the optical assembly comprises a prism.

20. The method of claim 17, wherein the optical assembly comprises an optical grating.

* * * * *